US011013864B2

(12) United States Patent
Bowman et al.

(10) Patent No.: US 11,013,864 B2
(45) Date of Patent: May 25, 2021

(54) SMALL UNIT DOSAGE PLUNGER ROD STOPS

(71) Applicant: SHIRE HUMAN GENETIC THERAPIES, INC., Lexington, MA (US)

(72) Inventors: Steve Bowman, Lexington, MA (US); Chase Fetzer, Lexington, MA (US); Richard Braga, Lexington, MA (US); Evi Shiakolas, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 28 days.

(21) Appl. No.: 15/804,439

(22) Filed: Nov. 6, 2017

(65) Prior Publication Data

US 2018/0126085 A1 May 10, 2018

Related U.S. Application Data

(60) Provisional application No. 62/417,862, filed on Nov. 4, 2016.

(51) Int. Cl.
*A61M 5/315* (2006.01)

(52) U.S. Cl.
CPC .... *A61M 5/31501* (2013.01); *A61M 5/31505* (2013.01); *A61M 5/31515* (2013.01);
(Continued)

(58) Field of Classification Search
CPC ............ A61M 5/31501; A61M 5/3195; A61M 5/31578; A61M 5/31548; A61M 5/31515; A61M 5/31505
See application file for complete search history.

(56) References Cited

U.S. PATENT DOCUMENTS 3,770,026 A * 11/1973 Isenberg ........... A61M 5/31525
141/2
4,073,321 A * 2/1978 Moskowitz ....... A61M 5/31501
141/27
(Continued)

FOREIGN PATENT DOCUMENTS

DE   202016104344 U1   8/2016
KR   20-0166416 Y1    2/2000
WO   2012/148717 A1   11/2012

OTHER PUBLICATIONS

International Search Report and Written Opinion dated Feb. 19, 2018, for Appl. PCT/US2017/060177, filed Nov. 6, 2017 (17 pages).
(Continued)

*Primary Examiner* — Theodore J Stigell
(74) *Attorney, Agent, or Firm* — Troutman Pepper Hamilton Sanders LLP

(57) ABSTRACT

Plunger rod stops attach to existing syringes to limit the range of motion of the plunger, thereby to precisely control the amount of liquid that can be expelled from the syringe when the plunger rod stop is in place. In some embodiments, plunger rod stop devices generally include a body configured to attach to the plunger, and a stand-off extending from the body, configured to contact the finger flange when the plunger is depressed. In other embodiments, the plunger rod stop attaches to the finger flange or other fixed component of the syringe and the stand-off is configured to contact the plunger or plunger rod. Methods of the invention involve using the devices to interfere with the range of motion of the plunger, then reconfiguring or removing the device to allow the plunger to be moved a predetermined length, which corresponds to a precise dosage amount.

10 Claims, 35 Drawing Sheets

(52) U.S. Cl.
CPC .... *A61M 5/31548* (2013.01); *A61M 5/31578* (2013.01); *A61M 5/31595* (2013.01)

(56) References Cited

U.S. PATENT DOCUMENTS

| | | |
|---|---|---|
| 5,318,544 A | 6/1994 | Drypen et al. |
| 5,662,098 A * | 9/1997 | Yoshida ................ B05B 1/3436 |
| | | 128/200.22 |
| 5,951,526 A | 9/1999 | Korisch et al. |
| 5,975,355 A | 11/1999 | Cecala et al. |
| 2005/0215957 A1 | 9/2005 | Hynes |
| 2011/0040280 A1 | 2/2011 | Ijitsu et al. |
| 2015/0157801 A1 * | 6/2015 | Tran .................. A61M 5/31591 |
| | | 604/208 |

OTHER PUBLICATIONS

Search Report issued in corresponding European Patent Application No. 17867630.0 dated Oct. 8, 2020.

* cited by examiner 0.3mL Insulin Syringe (31G x 8mm needle)

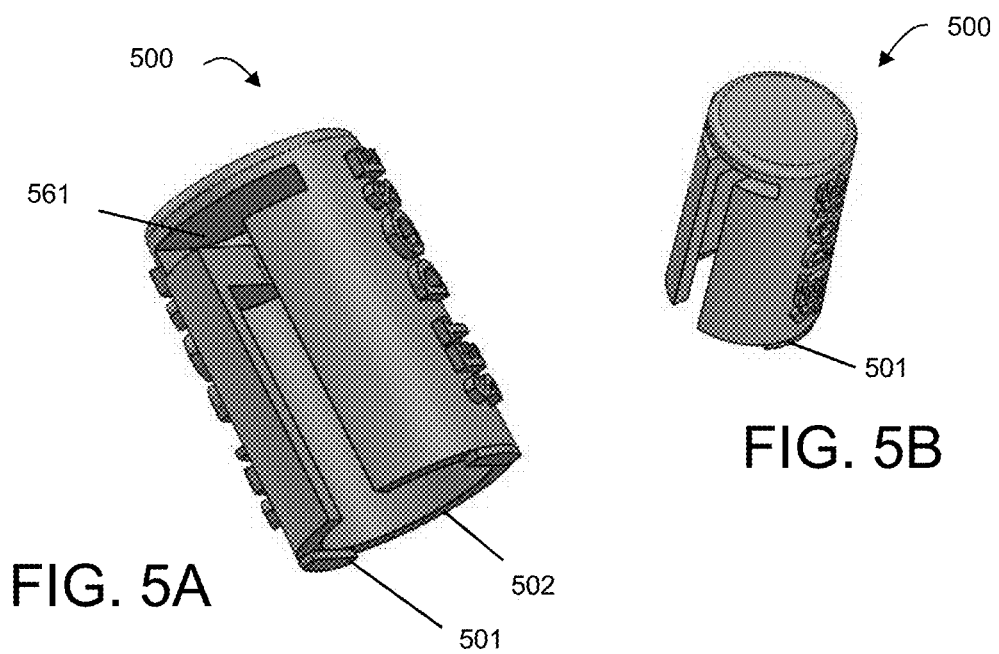

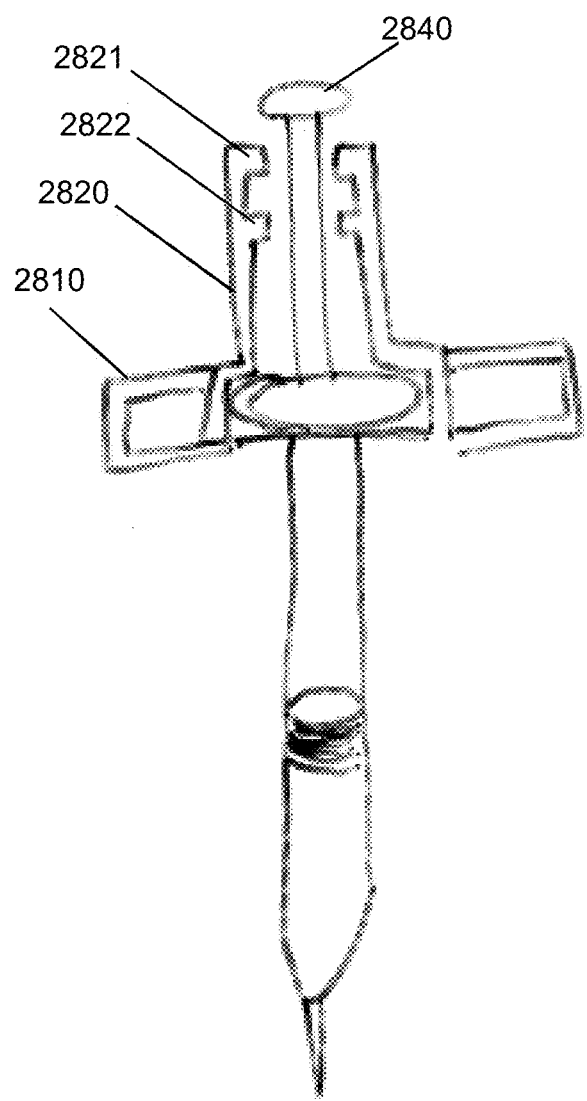
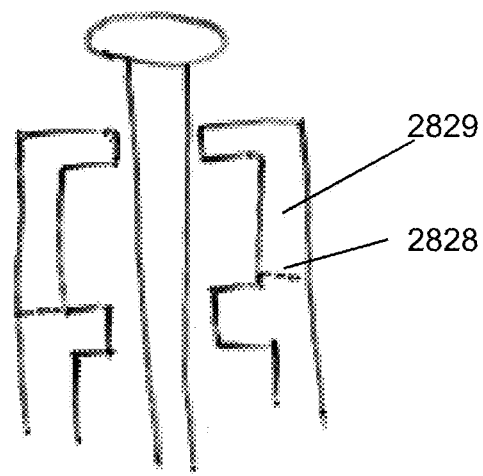
FIG. 28A
FIG. 28B

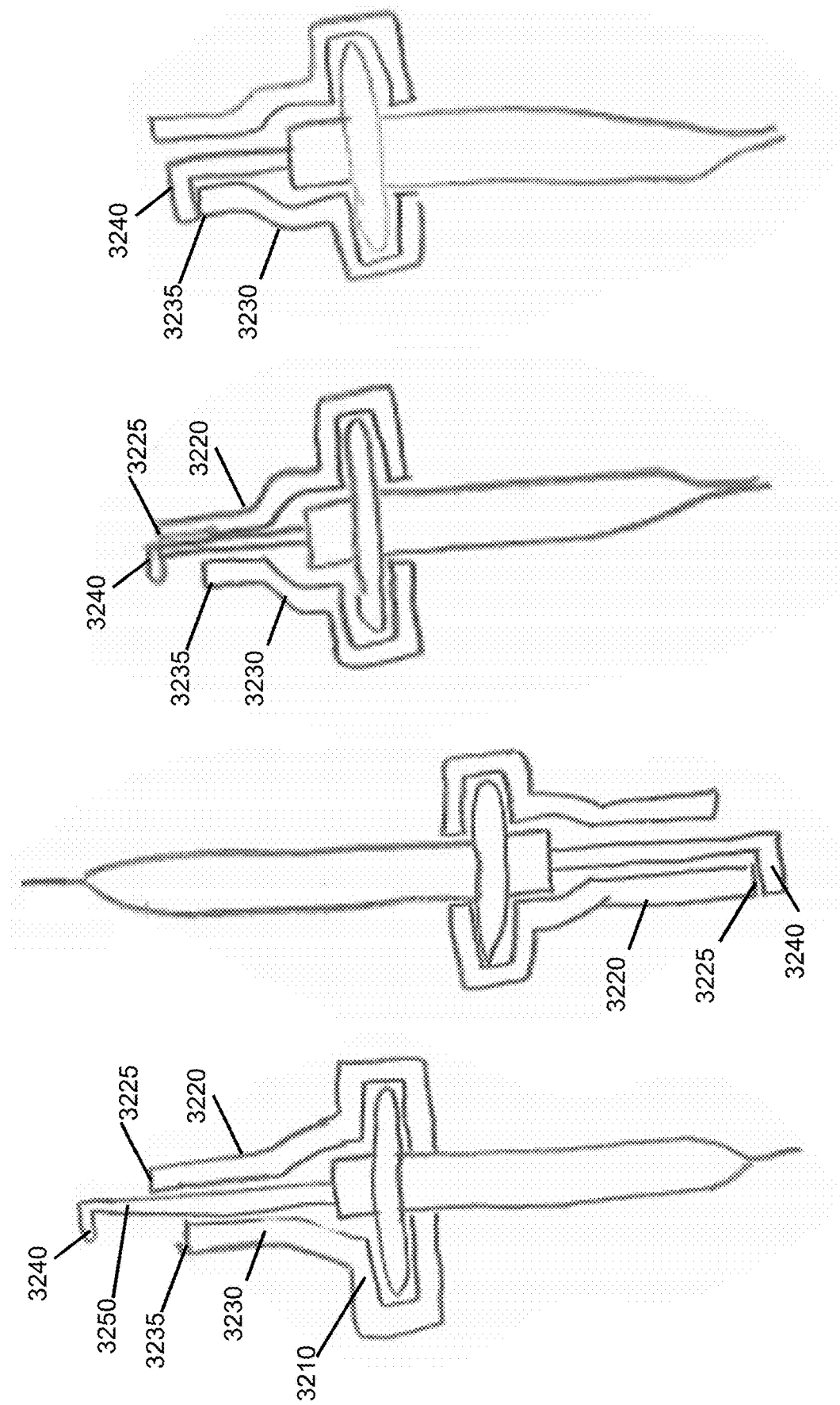

SMALL UNIT DOSAGE PLUNGER ROD STOPS

CROSS-REFERENCE TO RELATED APPLICATION(S)

This application claims the benefit of and priority to U.S. Provisional Application Ser. No. 62/417,862, filed Nov. 4, 2016, the contents of which are incorporated by reference in their entirety.

FIELD OF THE INVENTION

The invention generally relates to drug delivery devices, and in particular syringes and syringe attachments for providing defined small doses with high precision and accuracy.

BACKGROUND

Syringes are commonly used for delivering injectable medications. Generally a syringe includes a cylindrical chamber configured to contain a liquid medication, a needle at a distal end of the chamber, and a plunger at a proximal end of the chamber. The plunger rod is slidable within the chamber to push the liquid medication through the needle when a pressure is applied to the plunger. Syringes can be preloaded with a measured dosage of medication or they can be fillable by a healthcare professional, such as by drawing liquid in through the needle by pulling back on the plunger.

Although they are well-known in the medical field, conventional syringes are not particularly effective for delivering small dosages (e.g., less than 0.25 mL) of a drug. Syringes typically contain much larger volumes of liquid (up to several milliliters), and attempting to deliver a smaller amount than the full chamber can be challenging, even for an experienced healthcare professional. Doing so may result in incorrect dosing, leading to adverse healthcare outcomes. Additionally, syringes with premeasured amounts of liquid are limited in that they do not allow the healthcare professional to choose a particular dosage. Prior art syringes are thus limited both in the ability to deliver small doses and the flexibility of delivering variable amounts of medication.

SUMMARY

The invention provides plunger rod stops that attach to existing syringes to limit the range of motion of the syringe plunger rod, thereby precisely controlling the amount of liquid that can be expelled from the syringe. Various embodiments of the plunger rod stop devices and systems are disclosed. A common feature of the various embodiments is that a precisely sized device is attached to the syringe to bear against the plunger and prevent it from being depressed all the way. The plunger rod stop device is then reconfigured, rotated, removed, or replaced in order to allow the plunger to move a predetermined length, before contacting another bearing surface (or the same bearing surface in a different location). The difference in position between the first and second surfaces determines the precise distance that the plunger travels, which corresponds to a measured dosage that is less than the full volume of the syringe barrel.

A preferred plunger rod stop includes an elongated member that is configured to interfere with the range of motion of the syringe plunger rod when the stop is attached. The elongated member has a bearing surface that stops the plunger rod from fully depressing into the barrel. The plunger rod stop is removable from the barrel of the syringe, which allows a second plunger rod stop to be attached. A precise volume can thus be injected based on the difference in size between the two plunger rod stops.

The plunger rod stop includes an attachment element that attaches to either the plunger or the finger flange of a syringe. The plunger rod stop device also includes an elongated member with a bearing surface distal to the attachment element. The distance between the attachment element and the distal bearing surface dictates the range of motion of the syringe plunger rod. As will be described with respect to the figures below, an elongated member that has a greater length limits the range of motion of the plunger rod more than an elongated member having a shorter length. In some embodiments, the plunger rod stop is reconfigurable to provide two different lengths (between the bearing surface and the attachment element), and the difference between the two lengths determines the dosage volume. In other embodiments, the plunger rod stop is attached and the syringe is "set" by depressing the plunger until the bearing surface engages, and then the plunger rod stop is removed to allow the plunger to be fully depressed, releasing the remaining volume from the syringe. In other embodiments, two plunger rod stops having different lengths can be used in succession such that the difference between the lengths can be calibrated to deliver a particular dosage. For example, a first plunger rod stop is placed on the syringe, and the plunger is depressed until it contacts the stop. Without moving the plunger, the first plunger rod stop is removed and replaced by a second plunger rod stop, thereby leaving a small gap between the plunger and the second plunger rod stop, and the needle is inserted into a patient. (Alternatively, the syringe could be inserted into a patient, and then the first plunger rod stop could be replaced.) The plunger is then depressed to a second position, defined by the second plunger rod stop. An amount of fluid from the syringe is expelled based on the distance between the two plunger rod stop positions. With a variety of plunger rod stops with elongated members of different lengths, a user can maintain precise control over the fluid dosage. Plunger rod stops having small differences in length can be used to deliver very small dosages that would not be possible without the use of the plunger rod stops. Additional embodiments are discussed below.

Aspects of the invention involve plunger rod stop devices for modifying a syringe. The plunger rod stop devices include a body configured to attach to either a plunger of the syringe or a fixed element of the syringe, such as the finger flange or the barrel. The plunger rod stop devices also include a stand-off extending from the body, which is configured to contact another part of the syringe when the plunger is depressed. In embodiments where the plunger rod stop device attaches to the plunger, the stand-off is configured to contact the fixed element, such as the finger flange or barrel; and in embodiments where the plunger rod stop device attaches to the fixed element, such as the finger flange or barrel, the stand-off is configured to contact the plunger. Contact with the plunger or fixed element prevents the plunger from being depressed beyond a predetermined position.

In embodiments, the body comprises a resilient material, such as a resin. The body may include a recessed area for receiving the plunger or the fixed element. The recessed area may include a crush rib or snap fitting for securing the plunger or fixed element.

In certain embodiments, the stand-off is molded to the body. In other embodiments, the stand-off is detachable from the body. The length of the stand-off may be adjustable, and the device may include a dial configured to move the position of the stand-off. In some embodiments, the device includes more than one stand-off.

Related aspects of the invention involve a plunger rod stop device for modifying a syringe. The plunger rod stop is configured to deliver a measured dose that is less than a full volume of the barrel of the syringe. The plunger rod stop device includes a cylindrical body made of a resilient material. The plunger rod stop device has a top surface, a recessed area beneath the top surface configured to receive the plunger of the syringe such that the top surface substantially covers the plunger, and a bottom edge. The plunger rod stop device also includes a stand-off extending axially from the bottom edge, the stand-off having a bearing surface distal from the bottom edge of the cylindrical body. When the plunger rod stop device is oriented in a first rotational orientation with respect to the finger flange of the syringe, and the plunger is depressed, the bearing surface contacts the finger flange thereby preventing the plunger from being depressed beyond a first position. When the plunger rod stop device is oriented in a second rotational orientation with respect to the finger flange and the plunger is depressed, the bottom edge of the cylindrical body contacts the finger flange thereby preventing the plunger from being depressed beyond a second position. The first position and the second position are different, and the distance between them (and thus the distance that the plunger can be depressed) determines a dosage volume.

In certain embodiments, the first position corresponds to a first volume of liquid remaining in the barrel, and the second position corresponds to a second volume of liquid remaining in the barrel. The dose of liquid is the difference between the first volume and the second volume. The measured dose of liquid may be less than 0.3 ml, such as between 5 µl and 75 µl.

In some embodiments, the cylindrical body is made of a resin material. The recessed area includes a crush rib or snap fitting for securing the plunger. The stand-off may be molded to the cylindrical body, or it may be removable from the cylindrical body. The plunger rod stop device may have multiple stand-offs. The length of the stand-off may be adjustable or it may be rigid. In embodiments where the length of the stand-off is adjustable, the adjustment can be made by rotating a dial.

In a related aspect, the invention involves a method for delivering a dosage of a liquid from a syringe. The method includes attaching to a syringe a plunger rod stop that has a cap configured to attach to a plunger of the syringe. The plunger rod stop also has an elongated member with a first bearing surface that is a first length from the cap and a second bearing surface that is a second length from the cap. The plunger rod stop is positioned such that the first bearing surface is aligned with a finger flange of the syringe when the plunger is depressed. The method further involves depressing the plunger until the first bearing surface contacts the finger flange; then repositioning the plunger rod stop so that the first bearing surface is not in contact with the finger flange without moving the plunger with respect to the finger flange; and then depressing the plunger until the second bearing surface contacts the finger flange, thereby delivering a measured volume of liquid corresponding to the difference between the first length and the second length.

In certain embodiments, the syringe is inserted into a patient prior to the second step of depressing the plunger. The step of repositioning the plunger rod stop may involve rotating the plunger rod stop with respect to the syringe. In other embodiments the elongated member is detachable from the plunger rod stop, and repositioning the plunger rod stop involves removing the elongated member from the plunger rod stop. In other embodiments, repositioning the plunger rod stop comprises turning a dial.

In certain aspects, the disclosure relates to a system for modifying a syringe to deliver a measured dose that is less than a full volume of the syringe's barrel. The system includes a first plunger rod stop. The first plunger rod stop includes an attachment clip configured to removably attach to a barrel or flange of the syringe and an elongated member extending proximally from the attachment clip. The elongated member has a bearing surface configured to bear against a plunger of the syringe when the attachment clip is attached to the barrel or flange, thereby preventing the plunger from being depressed past a first position with respect to the barrel.

The system further includes a second plunger rod stop substantially similar to the first plunger rod stop. The elongated member of the second plunger rod stop has a length that is shorter than a length of the elongated member of the first plunger rod stop, such that the bearing surface of the second plunger rod stop prevents the plunger from being depressed past a second position with respect to the barrel. Depressing the plunger from the first position to the second position causes a measured dose of liquid contained in the barrel to be expelled from the barrel.

In certain embodiments, the attachment clip is configured to attach to a finger flange on the syringe barrel. The attachment clip may include a substantially flat surface disposed perpendicularly to the plunger rod when the attachment clip is attached to the barrel. The elongated member may extend perpendicularly from the substantially flat surface of the attachment clip. The elongated member may have a concave shape configured to partially surround the plunger rod. In some embodiments, the bearing surface bears against a proximal end flange of the plunger.

In some embodiments, the first position corresponds to a first volume of liquid remaining in the barrel, and the second position corresponds to a second volume of liquid remaining in the barrel. The measured dose of liquid is the difference between the first volume and the second volume. The measured dose of liquid may be less than 0.3 mL, less than 100 µL, less than 10 µL, or less than 5 µL.

In some embodiments, the system further includes a third plunger rod stop substantially similar to the first and second plunger rod stops. The elongated member of the third plunger rod stop has a length that is shorter than the length of the elongated members of the first and second plunger rod stop. The third (and in some embodiments, fourth, fifth, etc.) plunger rod stop is useful for delivering another aliquot of liquid after the first aliquot has been injected, as will be described in greater detail below.

In a related aspect, the disclosure involves a method for delivering a dosage of a liquid from a syringe. The method involves attaching to a barrel of a syringe a first plunger rod stop including an elongated member having a first length. The method further includes depressing a plunger of the syringe until the plunger contacts a bearing surface on the elongated member of the first plunger rod stop. Then the method involves replacing the first plunger rod stop with a second plunger rod stop that has an elongated member having a second length that is shorter than the first length. The method also involves depressing the plunger until the plunger contacts a bearing surface on the elongated member of the second plunger rod stop, thereby delivering a measured volume of liquid corresponding to the difference in length between the first and second elongated members.

In some embodiments, each plunger rod stop attaches to a finger flange on the barrel. Each plunger rod stop may include an attachment clip comprising a substantially flat surface disposed perpendicularly to the plunger rod when the attachment clip is attached to the barrel. The elongated members may extend perpendicularly from the substantially flat surface of the attachment clip. The elongated members may have a concave shape configured to partially surround the plunger rod. The bearing surface may be configured to bear against a proximal end flange of the plunger.

In certain embodiments, when the plunger contacts the bearing surface on the elongated member of the first plunger rod stop, the plunger is in a first position and when the plunger contacts the bearing surface on the elongated member of the second plunger rod stop, the plunger is in a second position. The first position corresponds to a first volume of liquid remaining in the barrel, the second position corresponds to a second volume of liquid remaining in the barrel, and the measured volume of liquid is the difference between the first volume and the second volume. The measured volume of liquid may be, for example, less than about 0.3 mL, less than about 100 µL, less than about 10 µL, or less than about 5 µL.

In some embodiments, methods further include replacing the second plunger rod stop with a third plunger rod stop substantially similar to the first and second plunger rod stops. The elongated member of the third plunger rod stop has a length that is shorter than the length of the elongated members of the first and second plunger rod stop. The method may further involve depressing the plunger until the plunger contacts a bearing surface on the elongated member of the second plunger rod stop, thereby delivering a second measured volume of liquid corresponding to the difference in length between the second and third elongated members.

BRIEF DESCRIPTION OF THE DRAWINGS

FIGS. 5A-B show another embodiment of a plunger rod stop device.
FIGS. 28A-B and 29A-B show plunger rod stop devices that include elongated elements with a plurality of stops.
FIGS. 32A-D show a plunger rod stop and a syringe with a half-moon shaped plunger.

DETAILED DESCRIPTION

Figure 1:
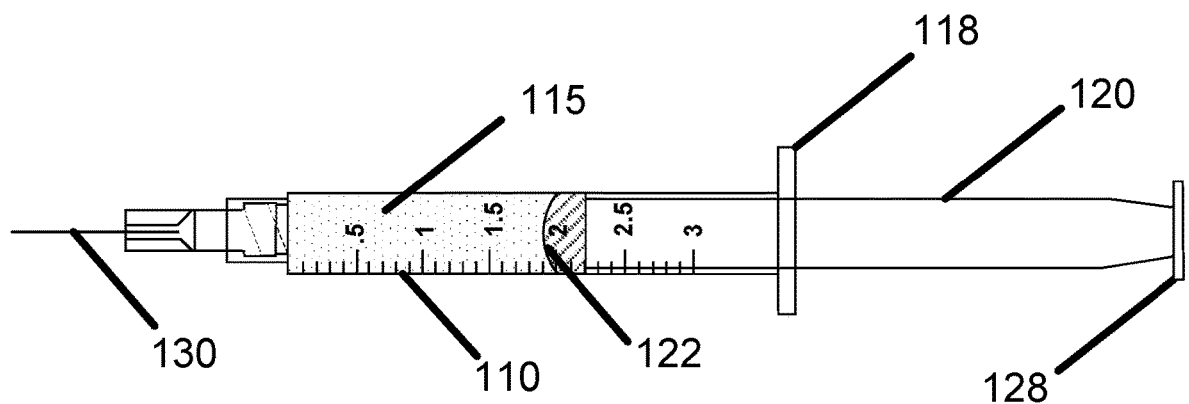
FIG. 1 shows a syringe for use with the plunger rod stops.

A plunger rod stop is an accessory for a syringe that allows precise drug delivery, including very small dosages (e.g., less than 0.25 mL) with high accuracy (e.g., within 5%). Plunger rod stops clip onto the outside of an existing prefilled or empty syringe and limit the range of motion of the syringe plunger to allow a small dosage output. The dosage can be fine-tuned based on the particular needs of the patient. Plunger rod stops allow a standard syringe to deliver dosages smaller than 0.3 mL, for example 5 µL or smaller.

Multiple plunger rod stops of different sizes can be used in conjunction to allow a user a wide range of variability in dosages. In use, a healthcare professional would first identify a desired dosage volume based on the particular needs of the patient. The healthcare professional would then select two plunger rod stops of different lengths, wherein the difference in lengths corresponds to the dosage volume. For example, if a desired dosage is 10 µL, the healthcare professional may select for example a 100 µL plunger rod stop and a 90 µL plunger rod stop. The 100 µL plunger rod stop is configured to prevent the plunger rod from sliding past the point where 100 µL of liquid remains in the syringe; and the 90 µL plunger rod stop is configured to prevent the plunger rod from sliding past the point where 90 µL of liquid remains in the syringe.

The 100 µL rod stop would be attached first, and the plunger would be depressed until it reaches the rod stop. The 100 µL rod stop would be removed and replaced by a 90 µL rod stop. The needle may then be inserted into the patient, and by pressing the plunger down from the 100 μL position to the 90 μL position, the syringe delivers 10 μL of fluid.

Plunger rod stops address the problem of prior art syringes that are ineffective for delivering precise and accurate small dosages to a patient. Plunger rod stops may be particularly useful for pediatric patients who may require small doses, but they are also useful for giving the healthcare professional greater control over dosage and making existing syringes more versatile. They can be used with empty or prefilled syringes, and since they fit on the outside of the syringe, they can modify dosage without breaching the primary container closure of the fluid drug product. They therefore provide a safer and easier alternative to methods that require transferring the fluid from one container to another.

Syringes on the market today generally do not allow delivery of very small doses. The smallest generally commercially available syringe is for insulin delivery for diabetic patients. But even those syringes only provide volumes as small as about 0.3 mL. In attempting to deliver smaller doses, for example 50 μL, the user may attempt to estimate a partial dosage, but such estimation is inaccurate and unreliable. Even a professionally trained healthcare professional would have trouble delivering a target dose of such a small volume without an unacceptably high degree of variability. However, by using plunger rod stops, even a non-professional can easily deliver a target dose as small as 10 μL without a significant degree of variability.

The plunger rod stops disclosed herein are readily modified and customizable based on the particular needs of the user. They are easily redesigned to fit any existing syringe configuration, whether prefilled or empty. In particular they are useful for modifying 0.3 mL BD insulin syringes with bore diameters of about 3.05 mm, which are commonly used for drug delivery.

By mixing and matching different combinations of the final product, the user can fine-tune the experience and modify volumes as needed to deliver a chosen dosage from 75 μl down to about 5 μl. Most of the embodiments described below are configured to deliver a drug in increments of 5 μl. This is especially useful for conditions that require variable dosing as the condition progresses or improves and the patient's needs change. The invention allows dosage variation with a high degree of precision with only contacting external surfaces of the syringe, not contacting the drug in any way.

FIG. 1 shows a syringe 100 for use with the invention. A syringe 100 generally includes a cylindrical barrel 110 that defines an inner lumen 115. The barrel 110 includes a finger flange 118 at its proximal end. The finger flange 118 provides a bearing surface against which a user can hold the barrel with one or more fingers while pushing or pulling the plunger 120. The barrel 110 has a needle 130 at its distal end, through which liquid may be drawn into the barrel 110 or expelled from the barrel 110.

At a proximal end of the barrel 110, the plunger rod 120 is slidable within the lumen 115. The plunger rod 120 includes a plunger tip 122, which forms a seal with the inner lumen 115 to define a proximal boundary of the inner lumen 115. When the syringe 100 is filled with a liquid, the plunger tip 122 prevents the liquid from exiting the barrel 110 through the proximal end of the lumen 115.

At the proximal end of the plunger rod 120 is a plunger 128, which forms a flange that can be pulled proximally to draw liquid into the barrel 110 through the needle 130 or pushed distally to expel liquid through the needle 130.

Generally, to fill the syringe 100, a healthcare professional starts with the plunger rod 120 fully inserted into the barrel 110 and places the end of the needle 130 into a liquid. The plunger rod 120 is then pulled proximally by the plunger 128 while the barrel 110 is held in place by the finger flange 118 until a desired amount of liquid has been drawn through the needle 130 into the barrel 110.

To eject the liquid from the syringe 100, such as for injection into a patient, the plunger rod 120 is pushed distally by the plunger 128. As the plunger rod 120 moves distally through the inner lumen 115, the plunger tip 122 maintains a seal with the barrel 110, forcing the liquid to leave the barrel 110 through the needle 130. The syringe 100 can be reusable or it can be a single-use device. In some embodiments, rather than drawing liquid into the syringe, the syringe comes preloaded with a measured volume of liquid.

Figure 2:
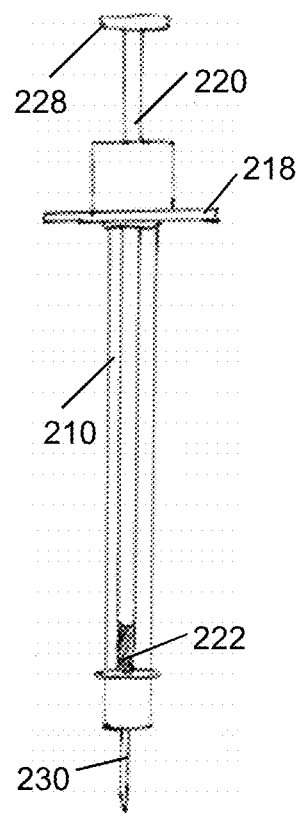
FIG. 2 shows a syringe for use with the plunger rod stops.

FIG. 2 shows a 0.3 mL insulin syringe 200 with an 8 mm needle. In general the syringe 200 delivers 0.3 mL of insulin when the plunger 228 is fully depressed, expelling the entire contents of the barrel 210 through the needle 230. According to the present invention, the syringe 200 can be modified to deliver a smaller dosage with precision and accuracy.

Figure 3A:
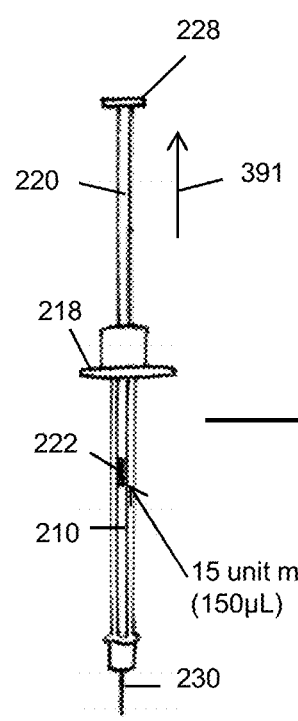
FIGS. 3A-C show attaching a plunger rod stop to a syringe.
Figure 3B:
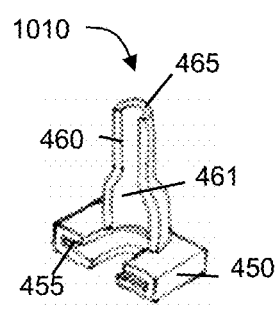
Figure 3C:
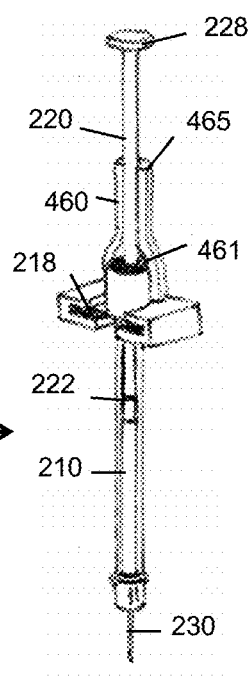

FIGS. 3A-C show steps for modifying the syringe 200 to deliver a smaller dosage. In this example, the desired dosage is one unit of 10 μL. In FIG. 3A, the plunger rod 220 is drawn proximally (indicated by arrow 391) to fill the barrel 210 with 15 units (i.e., 150 μL). The plunger tip 222 is shown at the 15 unit position on the barrel 210. FIG. 3B shows a 10-unit plunger rod stop 1010 to be inserted onto the syringe. The plunger rod stop 1010 includes an attachment clip 450 with a slit 455 that fits over the finger flange 218 of the syringe 200. The plunger rod stop 1010 also includes an elongated member 460 extending perpendicularly from the attachment clip 450.

As shown in FIG. 3C, the elongated member 460 is substantially semi-cylindrical with a cavity 461 configured to receive a distal portion of the barrel 210 and a portion of the plunger rod 220. The elongated member 460 also includes a proximal bearing surface 465 that bears against the plunger 228 when the plunger rod 220 is slid distally into the barrel 210.

Figures 4A, 4B, 4C, 4D:
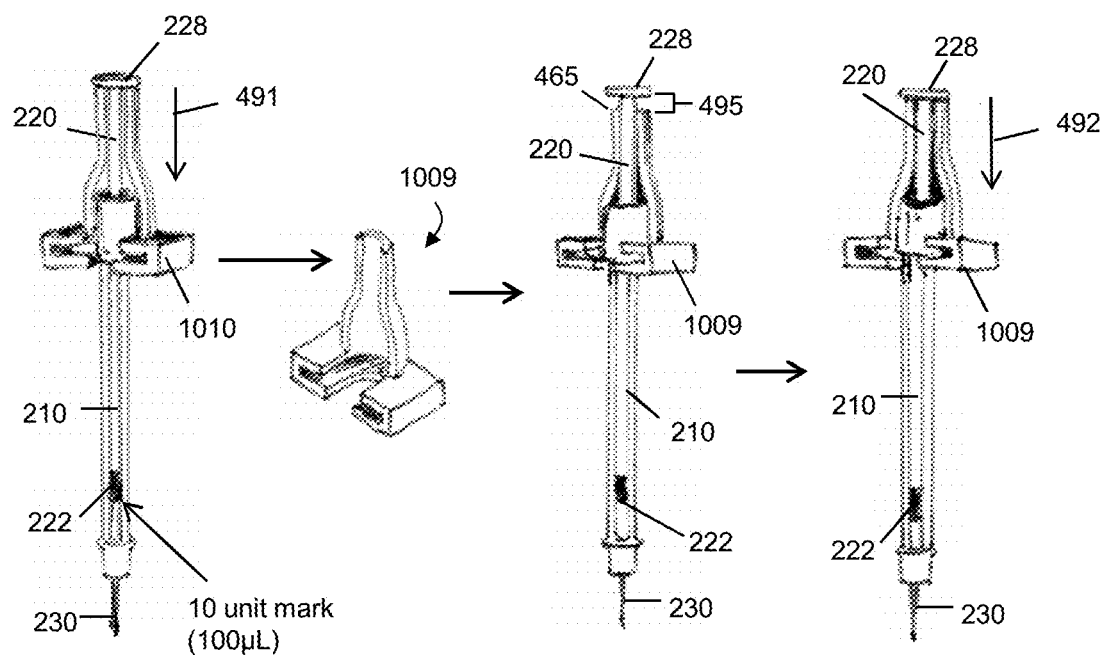
FIGS. 4A-D show replacing a plunger rod stop with a second plunger rod stop and delivering a precise volume of liquid with the syringe.

As shown in FIG. 4A, the bearing surface 465 limits the range of motion of the plunger rod 220 to prevent the full volume contained in the barrel 210 from being expelled. The length of the elongated member 460 determines the volume of liquid that can be expelled because the length of the elongated member 460 shortens the length that the plunger rod 220 is free to move within the barrel 210. In the example shown, the plunger 228 is depressed (indicated by arrow 491) until it reaches the bearing surface 465 of the elongated member 460 to expel air and excess liquid from the barrel 220. The plunger tip 222 is positioned at the 10-unit position, indicating that 10 units (100 μL) of liquid remain in the barrel 220.

Next, without moving the plunger 220, the 10-unit plunger rod stop 1010 is removed from the syringe and replaced with a 9-unit plunger rod stop 1009, as shown in FIGS. 4B-D. The elongate member of the 9-unit plunger rod stop 1009 is shorter than that of the 10-unit plunger rod stop, leaving a 1-unit gap 495 between the plunger 228 and the bearing surface 465, as indicated in FIG. 4C. The needle 230 may then be inserted into a patient and the plunger 228 may be depressed (in the direction indicated by arrow 492) until it abuts with the bearing surface 465 of the 9-unit plunger rod stop. By moving the plunger 228 from the 10-unit position to the 9-unit position, 1 unit (or 10 µL) of liquid is injected by the needle 230.

The procedure described above with respect to FIGS. 2-4D is exemplary only, and a person of ordinary skill in the art would appreciate other similar uses for the plunger rod stops for injecting small dosages of liquids. The quantities and unit sizes may be changed, for example. Plunger rod stops are capable of expelling very small measured volumes from a syringe, such as 100 µL, 20 µL, 5 µL, or smaller.

In some embodiments, only one plunger rod stop need be used rather than two. For instance, in the example described above, if the user desired to inject 100 µL instead of 10 µL, the procedure could be performed with only the 10-unit plunger rod stop. The steps would be carried out the same as described above, except after the plunger 220 was placed in the 10-unit position, the 10-unit plunger rod stop would simply be removed, and the remaining volume in the barrel 210 would be injected. In such an example, there is no need for the second plunger rod stop.

In examples where particularly small volumes of liquid are desired, it is beneficial to use two plunger rod stops (as shown in FIGS. 2-4D) and thereby inject the difference between the two volumes (in that case, 1 unit). Injecting a portion of the liquid in the barrel rather than the last unit remaining in the barrel generally gives greater precision.

In some embodiments, a set of plunger rod stops may include 2, 3, 4, 5, 6, 7, 8, 9, 10, 20, 30, or more plunger rod stops, each with different lengths. By combining two of the plunger rod stops in the method described above, a user can achieve any desired unit volume. Additionally, more than two plunger rod stops can be used in succession to deliver multiple aliquots of liquid from the same syringe without having to reload the barrel. For example, after using the 9-unit plunger rod stop (in FIGS. 4B-D), the healthcare professional could repeat the steps with an 8-unit plunger rod stop to deliver yet another 1-unit dosage. The steps can be repeated multiple times as necessary.

The plunger rod stops can be used for an injectable liquid of any viscosity, including but not limited to pain medication, insulin, steroids, and anesthetics. Plunger rod stops are useful in non-medical contexts as well, for example for measuring aliquots of a reagent in a laboratory setting, for measuring ingredients in cooking, or any other purpose that requires precise liquid measurements, particularly small volumes of liquid. While the plunger rod stops have been described as being particularly useful for delivering small doses that would otherwise not be possible with a standard syringe, plunger rod stops can also be scaled up to a larger size for delivering larger quantities of accurately and precisely measured liquid, for example, 1 mL, 2 mL, 5 mL, 10 mL, 50 mL, 100 mL, etc.

FIGS. 5A-B, 6A-6B, and 7A-7C show another embodiment of a plunger rod stop. The plunger rod stop 500 is an adapter that fits over the plunger rather than over the finger flange. The adapter is compatible with available insulin syringes, such as the BD 0.3 ml insulin syringe with ULTRA-FINE™ needle, available from Becton Dickinson (Franklin Lakes, N.J.).

As shown in FIGS. 5A-B, the plunger rod stop 500 is generally cylindrical with a slot 561 shaped to receive a plunger 528. The slot 561 forms a T-shape to secure the plunger 528 and proximal end of the plunger rod 520. The plunger rod stop 500 may have a snap fitting or similar connection mechanism to secure it in place over the plunger, or it may loosely fit over the plunger 528 so that it can be quickly and easily put on and taken off by a healthcare practitioner during use. The plunger stop rod 500 includes two standoffs 501 that protrude from the distal edge 502 of the cylinder. The height different between the distal edge 502 and the stand-offs 501 defines the dosage.

Figure 6A:
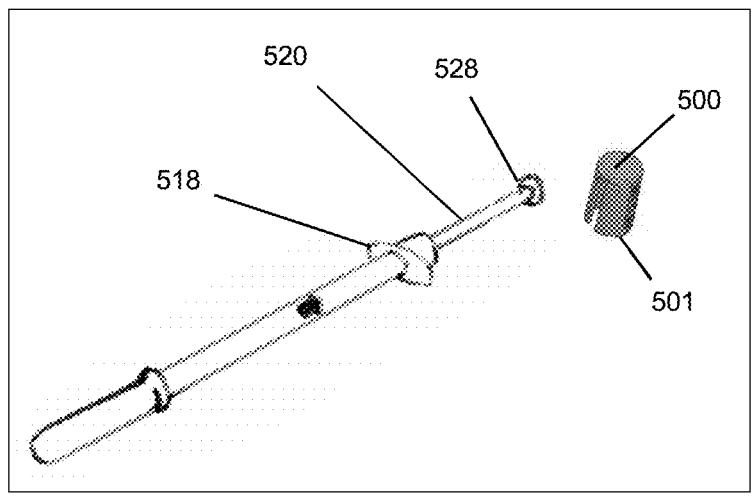
FIGS. 6A-B show the device of FIGS. 5A-B in use with a commercially available insulin syringe.
Figure 6B:
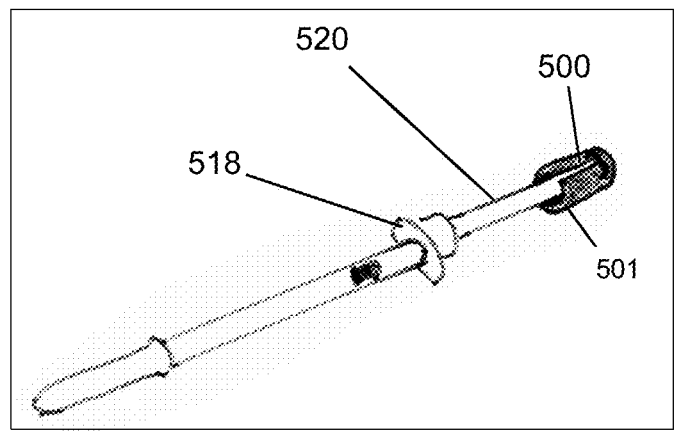

The plunger rod stop 500 is useful with syringes such as commercially available insulin syringes, as shown in FIGS. 6A and 6B. To use the plunger rod stop 500, the healthcare professional draws an amount of liquid into the syringe as shown in FIG. 6A. The amount of liquid should be greater than the desired dosage amount. The plunger stop rod 500 is then placed into position over the plunger 528 as shown in FIG. 6B. The slot of the plunger stop rod 500 has an inner diameter that allows it to rotate freely about the plunger 528 and plunger rod 520.

Figure 7A:
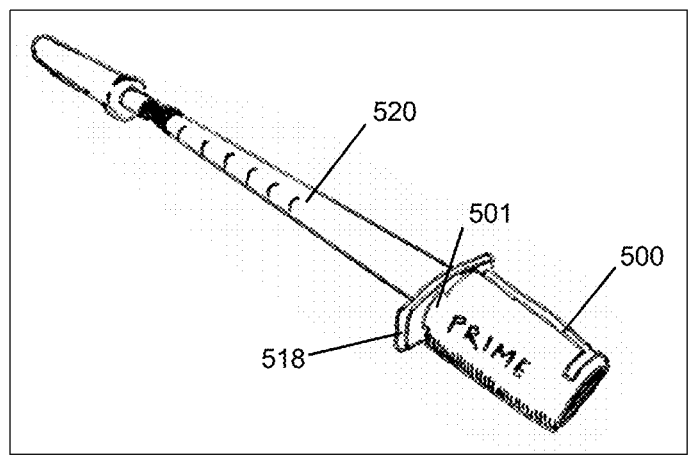
FIGS. 7A-C show the device of FIGS. 5A-B in use with a commercially available insulin syringe.
Figure 7B:
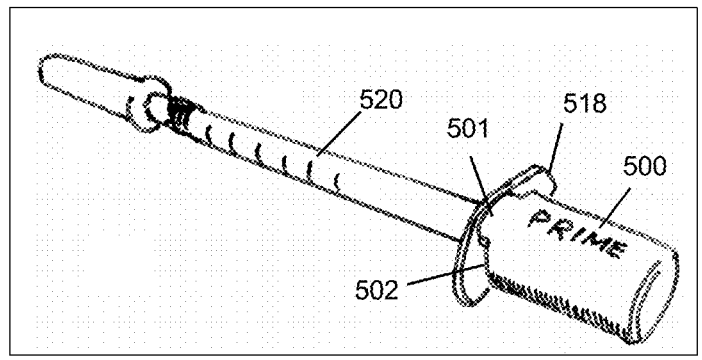
Figure 7C:
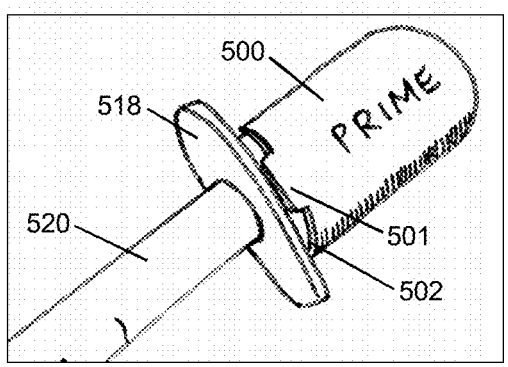

The plunger rod stop 500 is rotated so that the standoffs 501 are aligned with the finger flange 518. When the plunger is pressed down, the standoffs 501 contact the finger flange 518, preventing the plunger rod from sliding further into the barrel, as shown in FIG. 7A. The healthcare professional can thus prime the syringe by depressing the plunger 528 (via the plunger rod stop 500) until the standoffs 501 contact the finger flanges 518. Excess liquid will be expelled through the needle. The plunger rod stop 500 can then be rotated to move the standoffs 501 out of alignment with the finger flanges 518, as shown in FIGS. 7B and 7C.

The needle can then be inserted into the patient. The plunger 528 can be pressed down until the distal edge 502 of the cylinder contacts the finger flanges 518. Because it has been rotated, the standoffs 501 now project beyond the finger flanges 518. The volume of liquid expelled from the syringe corresponds to the distance between the edge of the standoffs 501 and the distal edge 502 of the cylinder. The standoffs 501 can be sized in order to allow a small measured dosage to be expelled through the needle, such as 100 µL, 50 µL, 20 µL, 10 µL, 5 µL, or less.

Figures 8A, 8B:
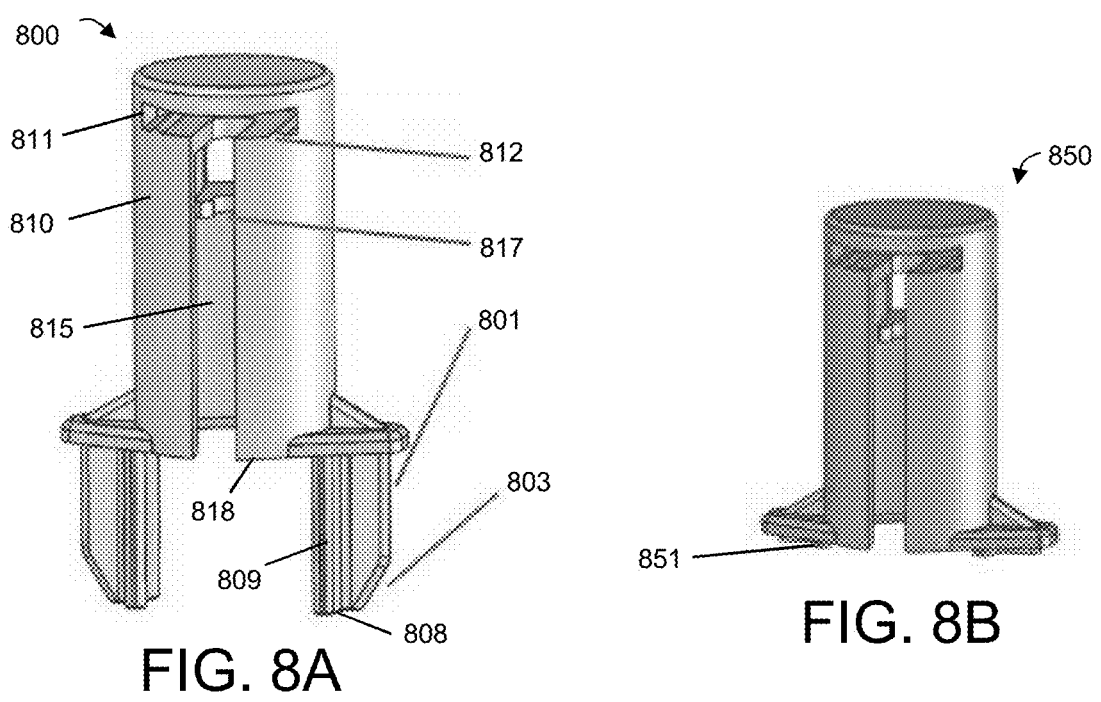
FIGS. 8A-B show a one-piece plunger rod stop device with stand-offs of different lengths.

Another one-piece plunger rod stop device 800 with longer stand-offs 801 is shown in FIG. 8A. The slot 811 in the upper portion of the cylinder 810 includes two crush ribs 812 that securely hold the plunger (not shown) in place with an interference fit. The presence of the crush ribs 812 eliminates movement between the plunger and the plunger rod stop device 800, ensuring greater dosage accuracy. A snap fitting 817 in the vertical recess 815 supports the plunger rod (not shown). The stand-offs 801 are tapered 803 to reduce the potential for pinching the user's hand during dosing. The stand-offs are strengthened by the presence of ribs 809 running along the stand-offs 801. The resiliency of the device 800 is important for precision dosing. The device can be made of a resin material such as DELRIN® available from DuPont.

One-piece designs are desirable because they do not require any assembly and are simple to use. Each one-piece device has a particular dosage that it is designed to administer, and that dosage is defined by the distance between the distal bearing surface 808 of the stand-offs and the bottom edge 818 of the cylinder 810. The one-piece device corresponds to one dosage volume, which helps to reduce user error that multi-piece device may be susceptible to. Since each one-piece device corresponds to only a particular dosage, several one-piece devices may be provided together in a kit in order to support a full dosage volume range.

A different embodiment of the 1-piece plunger rod stop device is shown in FIG. 8B. The device 850 is substantially the same as device 800 but with shorter stand-offs 851. Device 850 may for example be configured to deliver a dosage of 5 µl, whereas device 800 delivers a dosage of 75 µl.

Figures 9A, 9B, 9C:
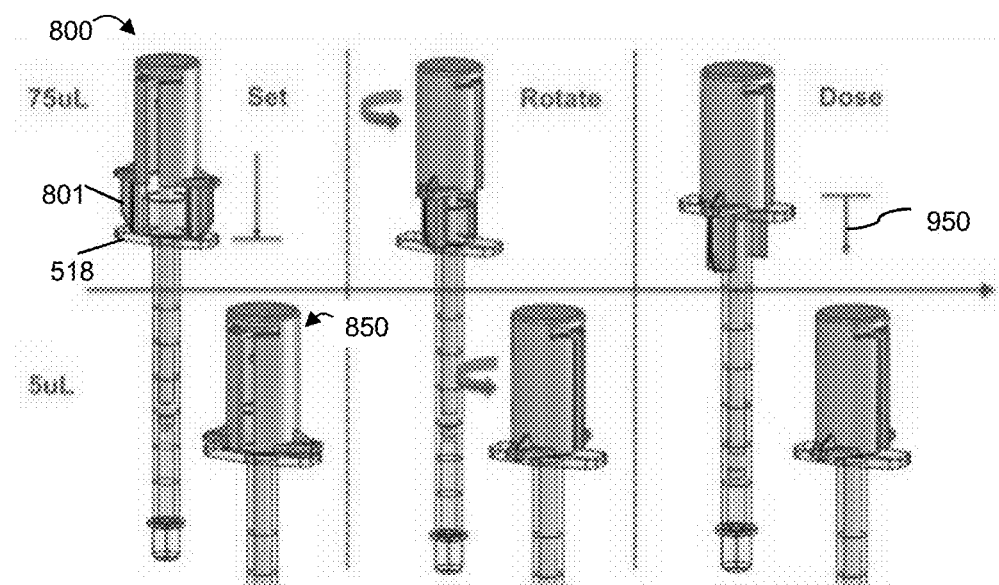
FIGS. 9A-C show a method of using the one-piece plunger rod stop devices of FIGS. 8A-B.

The manner of use of devices 800 and 850 is shown in FIGS. 9A-C. The one-piece plunger rod stop device 800 is attached to a standard insulin syringe by snapping the plunger rod into the snap fitting 817. The plunger is secured by the crush ribs 812. The device is rotated as needed so that the stand-offs 801 align with the finger flange 518 when the plunger is pushed down. In the first step, shown in FIG. 9A, the syringe is set by pressing the plunger down until the stand-offs 801 connect with the finger flange 518, preventing the plunger from moving further. A clinician performs the "set" step prior to inserting the needle into the patient.

The one-piece plunger rod stop 800 is then rotated to move the stand-offs 801 out of alignment with the two wings of the finger flange 518 as shown in the "rotate" step, depicted in FIG. 9B. This step can be performed either before inserting the needle into the patient, or after. The device should be rotated carefully so as not to translate the plunger up or down before dosing.

With the needle inserted into the patient, the "dose" step shown in FIG. 9C involves pushing the plunger downward until the bottom edge 818 of the cylinder 810 contacts the finger flange, which stops the plunger. As seen in FIG. 9C, the stand-offs 801 do not interfere with the downward movement of the plunger when they are not aligned with the finger flange 518. The dosage that is injected into the patient using this method thus corresponds to the distance that the plunger is depressed between the "set" step and the "dose" step (depicted as arrow 950), or in other words, the distance between the bottom edge 818 of cylinder 810 and the distal bearing surface 808 of stand-offs 801. The bottom half of FIGS. 9A-C show the same process with the device 850 having shorter stand-offs 851.

Figures 10A, 10B:
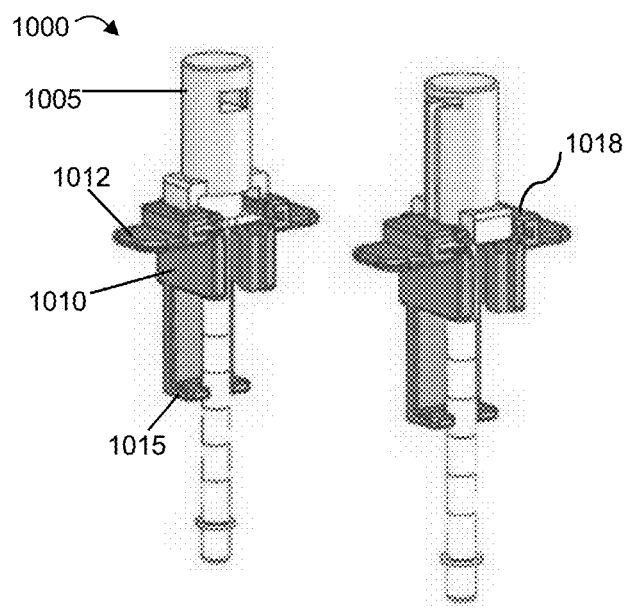
FIGS. 10A-B show a two-piece plunger rod stop system that includes a plunger rod stop and a stabilizer.

FIGS. 10A-B show a two-piece plunger rod stop system 1000 that includes a plunger rod stop 1005 and a stabilizer 1010. The stabilizer 1010 functions by attaching to a standard insulin syringe and providing a wider surface with which to contact the stand-offs. The stabilizer 1010 has a barrel attachment 1015 that connects to the barrel and two wings 1012 that cover each side of the finger flange. The two-piece system 1000 with the stabilizer 1010 retains much of the usability of the one-piece devices described above, with added stability and improved control. The added stabilizer 1010 is generic for all dosage volumes and can be used in conjunction with other one-piece plunger rod stop devices, such as those described above. FIG. 10A shows the plunger rod stop device in a first position, with the stand-offs connecting with a top surface of the stabilizer. FIG. 10B shows the plunger rod stop device turned 90 degrees and pushed down so that the stand-offs descend past the top surface 1018 of the stabilizer 1010.

Figures 11A, 11B, 11C, 11D:
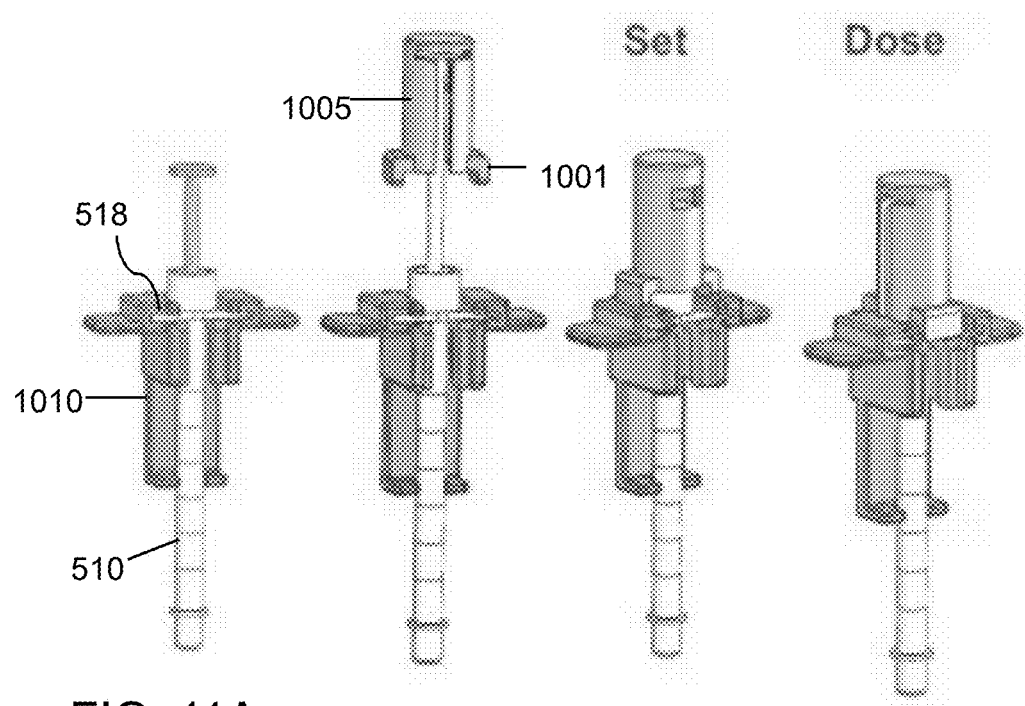
FIGS. 11A-D show the steps of using the two-piece plunger rod stop system with the stabilizer.

FIGS. 11A-D show the steps of using the two-piece plunger rod stop system 1000 with the stabilizer. The stabilizer 1010 is first attached to a syringe by fitting over the finger flange 518 and the proximal portion of the barrel 510 as shown in FIG. 11A. The stabilizer 1010 can be connected using a pressure fitting or other similar mechanism. The plunger rod stop device 1005 is then attached to the plunger as shown in FIG. 11B, before being pushed down into the "set" position in FIG. 11C, and providing the dosage by rotating and pushing the plunger into the "dose" position in FIG. 11D. As in other embodiments, the dosage amount is determined by the height of the stand-offs 1001. These steps are largely the same as the steps described above with respect to FIGS. 9A-C, except for the addition of the stabilizer 1010 to provide greater control to the user.

Figure 12A:
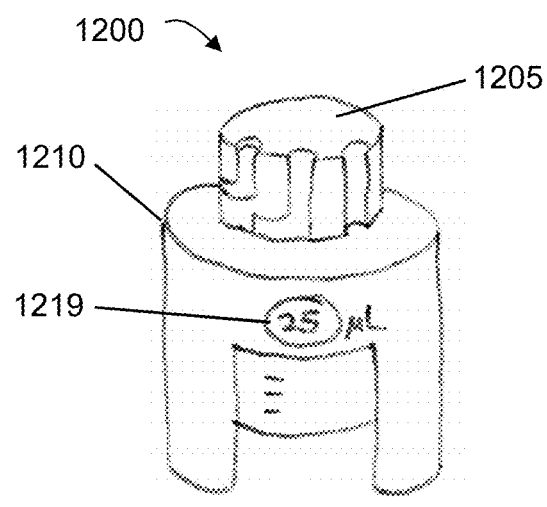
FIG. 12A shows a plunger rod stop device having a dial with slot channels.

Another plunger rod stop device 1200 is shown in FIG. 12A. The device 1200 is presented to the user as a one-piece device, although it includes a fixed piece 1210 and a dial 1205. The device can be connected to a syringe by inserting the plunger into a recessed area (not shown) similar to the recessed area shown in the embodiment of FIG. 8A. When a particular dosage is dialed in, the dosage amount appears through a window 1219 in the fixed piece 1210 to allow the user to easily calibrate the device 1200.

Figure 12B:
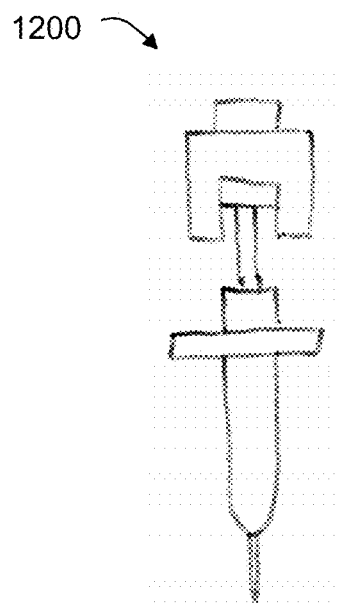
FIG. 12B shows the device of FIG. 12A attached to a syringe.
Figure 12C:
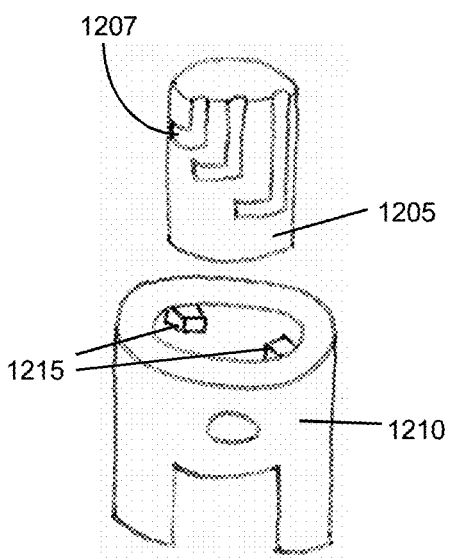
FIG. 12C shows an exploded view of the plunger rod stop device.

The slotted plunger rod stop design is shown attached to a syringe in FIG. 12B. An exploded view is shown in FIG. 12C, which shows how the two pieces are connected. The dial 1205 includes slot channels 1207 configured that receive teeth 1215 located in the inner recess of the fixed piece 1210. The dial can be adjusted by fitting the teeth 1215 into the desired slot channel 1207. A benefit of this adjustable design is that a kit can be provided with fewer parts to achieve the full dosage volume range.

Figure 13A:
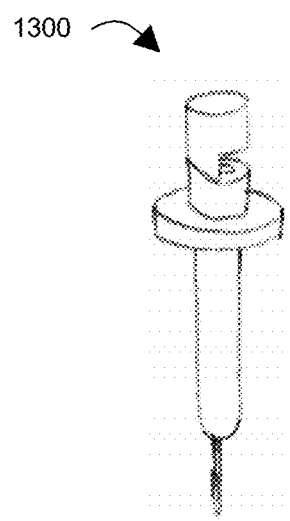
FIG. 13A shows a plunger rod stop device having a dial with a staircase connection, attached to a syringe.
Figure 13B:
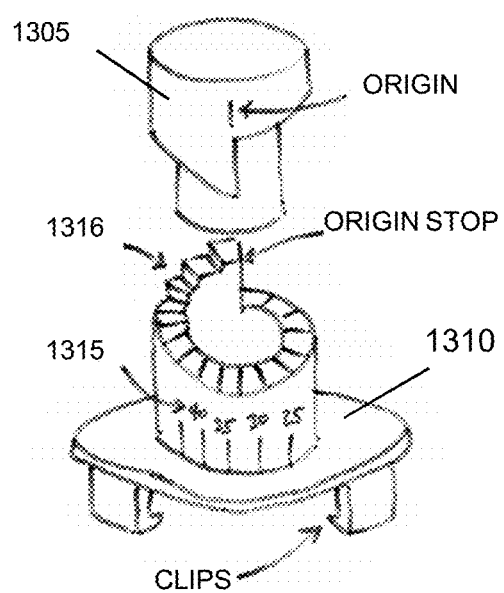
FIG. 13B shows an exploded view of the plunger rod stop device of FIG. 13A.

A variation of the dial design is shown in FIGS. 13A-B, which show a plunger rod stop device 1300 that can be dialed in to the desired dosage using a staircase mechanism. The device 1300 is shown in FIG. 13A connected to a syringe, and an exploded view of device 1300 is shown in FIG. 13B. Instead of the slot channel connection of device 1200, device 1300 has a staircase connection 1316 between the dial 1305 and the fixed piece 1310. Dosage marks 1315 are printed around the fixed piece 1310 and are indicated by a demarcation on the dial 1305 that points to the corresponding dosage that the device 1300 is set to. Such dial configurations reduce the number of parts required to support the full dosing volume range.

Figure 14A:
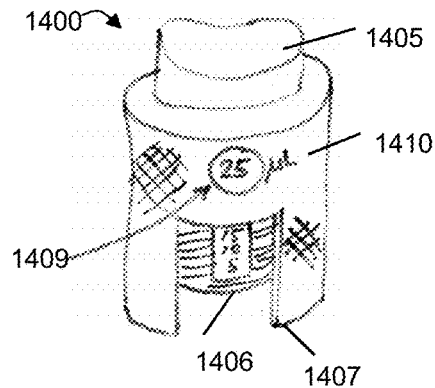
FIGS. 14A-C show a device with a dial that can be used to dial in the desired dosage volume.
Figure 14C:
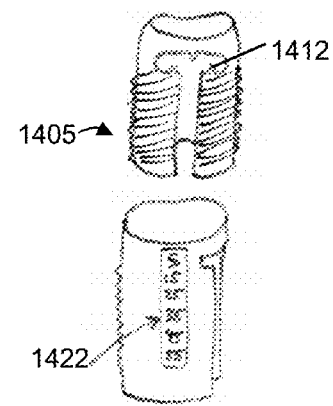
Figure 14B:
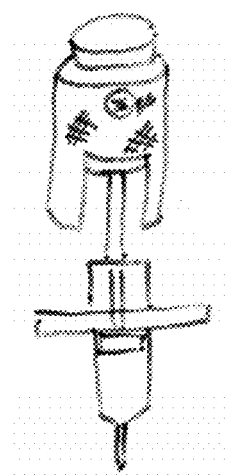

FIGS. 14A-C show a device 1400 with a dial 1405 that can be used to dial in the desired dosage volume. Rotating the dial 1405 causes the distance between the bottom surface 1406 of the dial and the stand-offs 1407 to increase or decrease. As the dial 1405 rotates, a dosage amount appears through a window 1409 in the fixed piece 1410 so that the user can easily calibrate the device. In some embodiments, the device provides audible or tactile feedback to indicate when a specific dose is dialed in. The device 1400 is shown attached to a syringe in FIG. 14B. Compared with the slotted embodiment of FIGS. 12A-C, the threaded dial of FIGS. 14A-C can provide even greater precision and a wider range of dosage volumes. As shown in FIG. 14C, the dial portion 1405 attaches to a plunger (not shown) with crush ribs 1412. In certain embodiments the thread pitch is two times the distance between each dosage demarcation. In the example shown, the dosage range is from 5 µl to 75 µl. The scale 1422 is indicated on the side of the dial and the dialed-in dosage is visible through the dose window 1409.

Figures 15A, 15B:
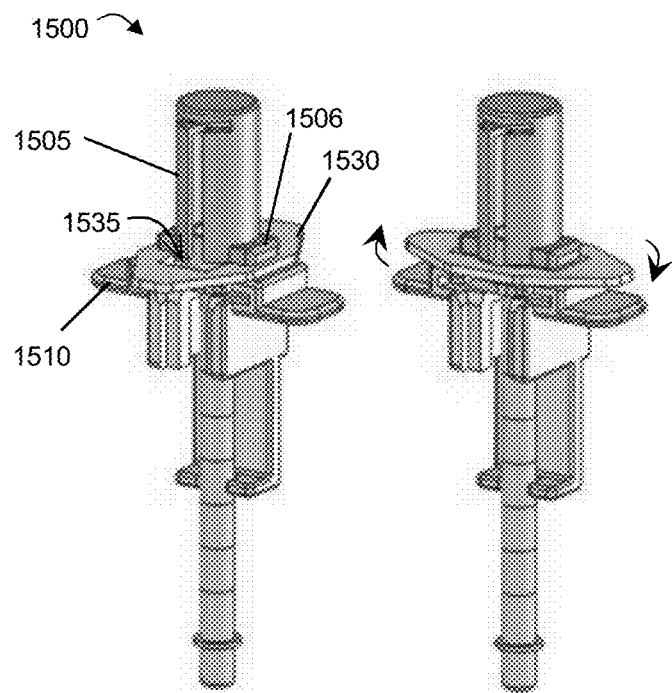
FIGS. 15A-B show a multi-piece plunger rod stop system that includes a stabilizer and a shim.

FIGS. 15A-B show a multi-piece plunger rod stop system 1500 that includes a stabilizer 1510 and a shim 1530. The thickness of the shim 1530 determines the dosage. The embodiment in FIGS. 14A-B is similar to that of FIG. 10A-B, except that the lower bearing surface of the plunger rod stop 1505 contacts the shim 1530 in the "set" step (FIG. 15A), and then the shim 1530 is repositioned (FIG. 15B), which allows the plunger to be pushed down in the "dose" step. The shim 1530 can be made of metal and can be precision machined to provide the exact height requirement for dosing volumes. In this embodiment, the mechanism for repositioning the shim 1530 involves rotating the shim 1530. The shim 1530 has a cutout 1535 that is substantially the same size and shape as the bottom surface of the plunger rod stop 1505 including the stand-offs 1506. The plunger rod stop 1505 can be pushed through the cutout 1535 only when properly aligned as in FIG. 15B. To set the device 1500 before dosage, the shim 1530 is rotated so that the cutout 1535 does not align (e.g., the orientation of the plunger rod stop 1505 and the cutout 1535 are perpendicular to each other as in FIG. 15A), and then plunger is pressed down until the bottom surface contacts the shim. In FIG. 15B, the shim 1530 is rotated as indicated by the two arrows. The rotation aligns the cutout 1535 so that the plunger can be depressed, causing the plunger rod stop device 1505 to pass through the cutout 1535, thereby releasing the dosage.

Figures 16A, 16B:
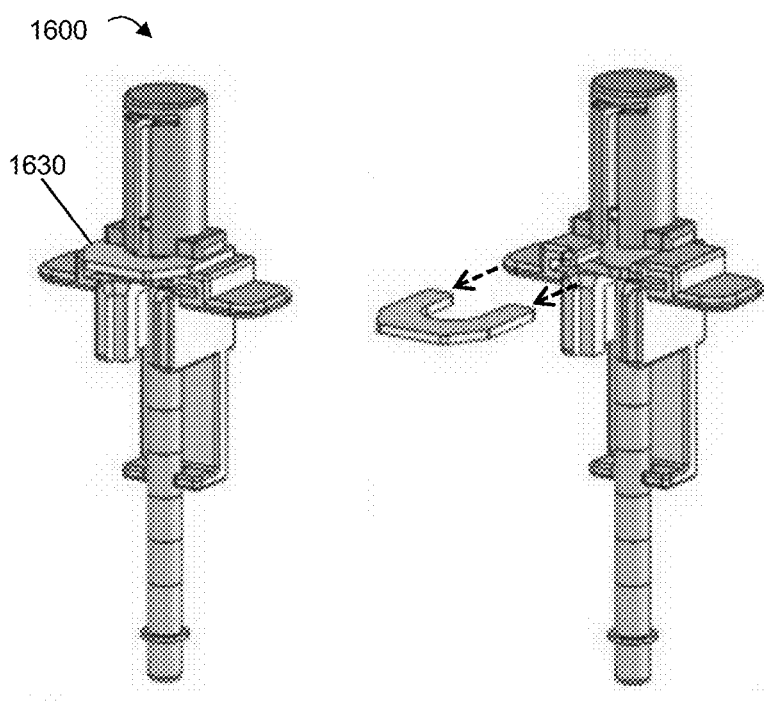
FIGS. 16A-B show another embodiment of a multi-piece plunger rod stop system that includes a stabilizer and a shim.

A similar embodiment is shown in FIGS. 16A-B, where instead of rotating, the shim 1630 is pulled out after the device is set. With the shim 1630 removed (FIG. 16B), the plunger can be pressed down to deliver the dosage. In both of the shim embodiments, the dosage volume is determined by the thickness of the shim. One metal shim corresponds to one dosage volume, so kits can be provided with several shims of varying thickness, along with one stabilizer piece and one plunger rod stop piece, to allow for delivery of a full dosing volume range.

Figures 17A, 17B, 17C:
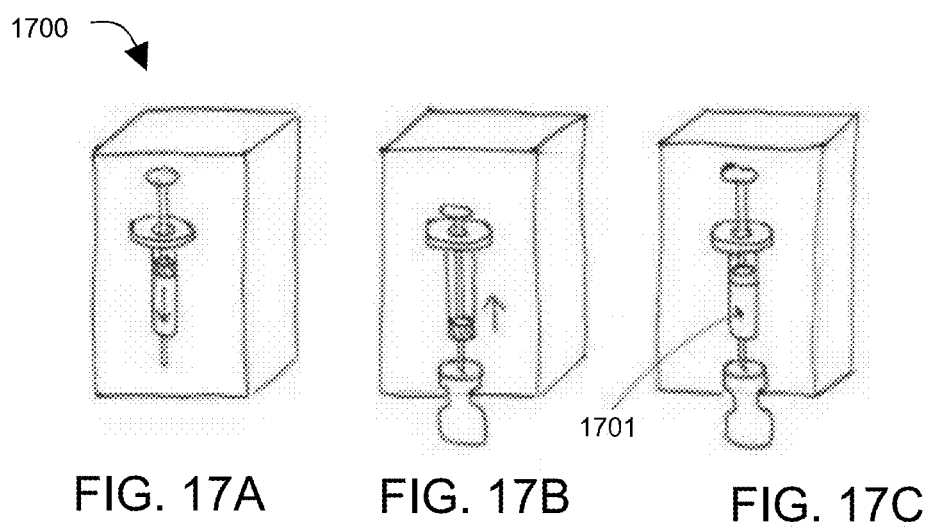
FIGS. 17A-C show a dosing fixture that allows a syringe to draw a desired amount into the barrel.

Another related device is the dosing fixture 1700 shown in FIGS. 17A-C. The dosing fixture 1700 allows a syringe to draw only a desired amount into the barrel. The syringe and the vial containing a liquid are attached and inserted into the dosing fixture. The syringe is purged until the plunger bottoms out, emptying the barrel. Next, the dosage is set using a micrometer adjustment. As the plunger is pulled back, the syringe is filled only to the amount determined by the micrometer adjustment. The syringe can then be removed from the dosing fixture, containing the exact dosage amount 1701. The needle is then inserted into the patient and the full dosage is delivered. The dosage fixture embodiment has the advantage of having no extra drug to inadvertently inject, thereby reducing the likelihood of overdose. There are also no additional components attached to the syringe during injection.

Figure 18:
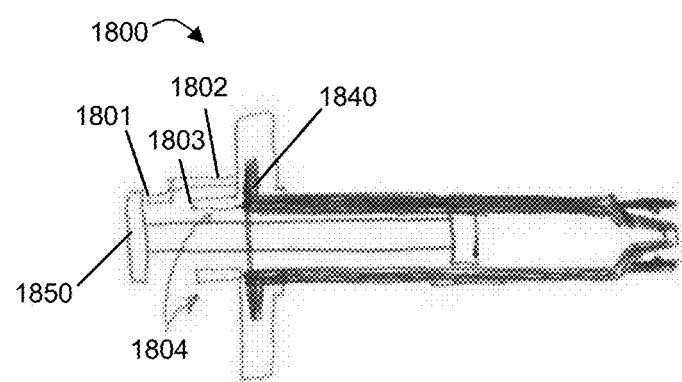
FIG. 18 shows a device that attaches to a finger flange and has a "stepped" design where two different bearing surfaces stop the movement of the plunger at two different locations.

As noted above with respect to FIGS. 3A-4D, the plunger rod stop device can be configured to attach to the finger flange rather than to the plunger. In either configuration, the plunger rod stop device acts to block the movement of the plunger and barrel with respect to one another. Another embodiment similar to that of FIGS. 3A-4D is shown in FIG. 18. The device 1800 attaches to the finger flange 1840 and has a "stepped" design where two different bearing surfaces stop the movement of the plunger at two different locations. The plunger 1850 is advanced until it contacts the proximal bearing surface 1801. The proximal bearing surface 1801 is located at an end of a tab 1802 which can be flipped, bent, broken off, or otherwise repositioned after the plunger has contact it, to free the plunger from the impediment of bearing surface 1801. Once tab 1802 is repositioned, the plunger can then be depressed until it contacts the distal bearing surface 1803 on impediments 1804. The distance between the proximal bearing surface 1801 and the distal bearing surface 1803 defines the metered dosage that device 1800 delivers. In certain embodiments, the device 1800 has multiple tabs of different lengths, which enable the device to deliver a variety of dosage volumes.

Figure 19A:
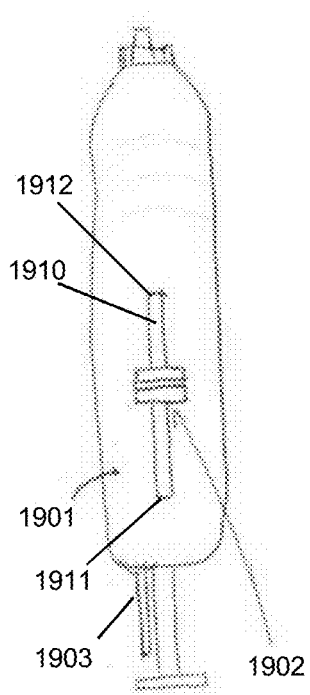
FIGS. 19A-C show an embodiment with a casing that fits over the syringe and a slider that advances a plunger stop.
Figure 19B:
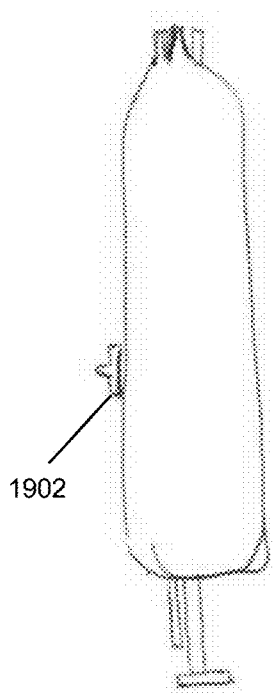
Figure 19C:
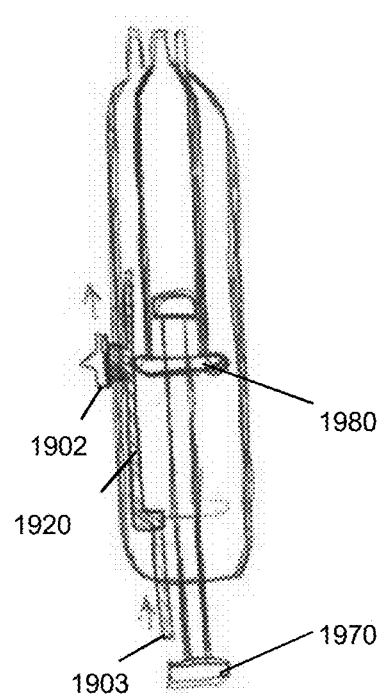

FIGS. 19A-C show a related embodiment in which a casing 1901 fits over the syringe and has a slider 1902 that advances a plunger stop 1903. As can be seen in the top view of the device 1900 shown in FIG. 19A, the slider can be positioned at any point in the range defined by the slot 1910. When the slider 1902 is pulled all the way back to point 1911, the plunger stop is fully extended, locking the plunger in place. The slider can be moved to various positions between points 1911 and 1912 that correspond to different dosages. When the slider 1902 is advanced all the way to point 1912, the plunger stop is fully retracted into the casing 1901, allowing the plunger complete range of motion. A scale (not shown) could be printed on the outside of the casing, indicating the corresponding dosage volumes. The side view of FIG. 19B shows that slider 1902 is raised above the surface of the casing 1901, which allows a user to manually advance the slider 1902 as needed.

FIG. 19C shows a cross-sectional view of the device 1900, revealing the internal mechanism that allows the slider to control the position of the plunger stop 1903. The slider 1902 is connected to a frame 1920, which is positioned close to the inside of the casing 1901 so that it is free to slide back and forth without interference from the finger flange 1980. The frame 1920 connects to the plunger stop 1903, which is positioned to align with the plunger 1970.

In a method of using device 1900, the slider 1902 is set to a first position and the plunger is advanced to contact the plunger stop 1903. The slider 1902 is then advanced to a second position. The difference between the first and second positions determines a dosage volume, as indicated by a scale printed on the outside of the casing (not shown). The plunger 1970 is then depressed until it contacts the plunger stop 1903 again, thereby expelling the desired volume.

Figure 20A:
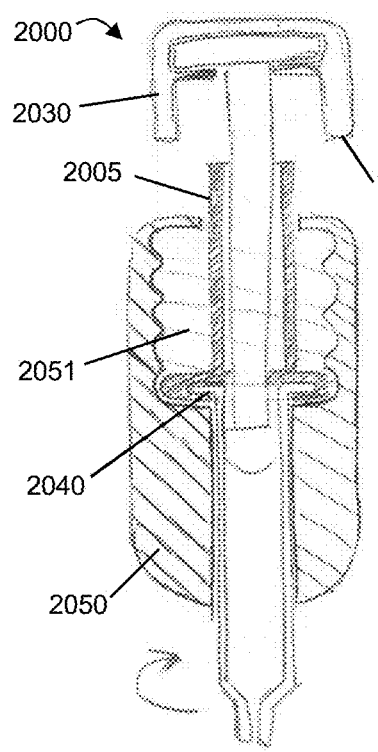
FIGS. 20A-C show a multi-part device with a sleeve that attaches to the finger flange and a body that fits over the sleeve.
Figure 20B:
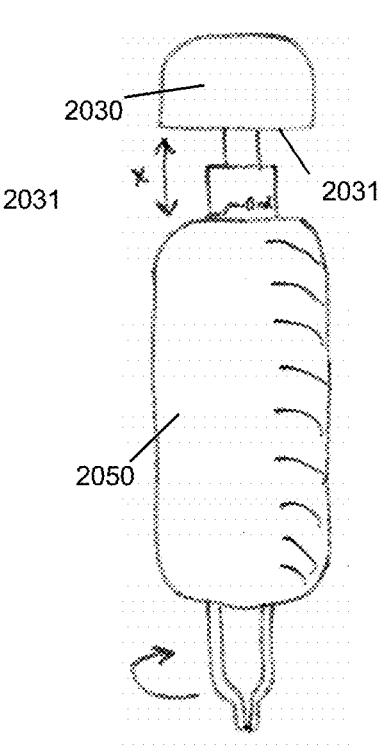
Figure 20C:
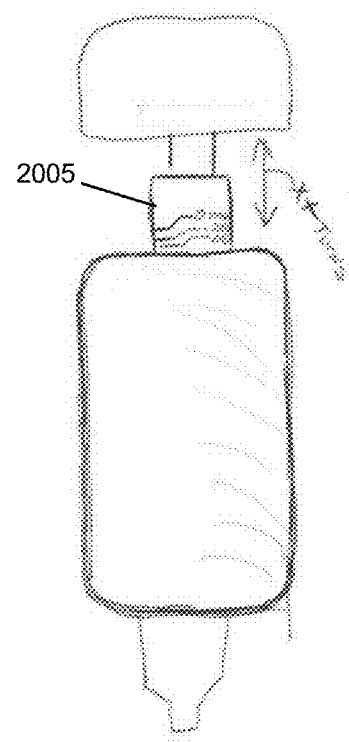

FIGS. 20A-C show a multi-part device 2000 with a sleeve 2005 that attaches to the finger flange 2040 of a syringe, a body 2050 that fits on the sleeve 2005. As shown in the cross-sectional view of FIG. 20A, the body 2050 connects with the sleeve 2005 via an internal threading 2051 that allows the body 2050 to be moved up and down with respect to the finger flange 2040 by rotating the body 2050. A plunger cap 2030 fits onto the plunger and includes a forward-facing circular bearing surface 2031. In FIG. 20B, the device is set to a first position indicated by distance "x". The plunger cap 2030 can be advanced until the bearing surface 2031 contacts the body 2050. As shown in FIG. 20C, the body can then be rotated a number of turns to a second position. The dosage volume can be determined based on a scale printed on the sleeve 2005. Once the body 2050 is in the second position, the plunger can be depressed until the bearing surface 2031 contacts the body 2050, thereby releasing the indicated dosage.

Figure 21A:
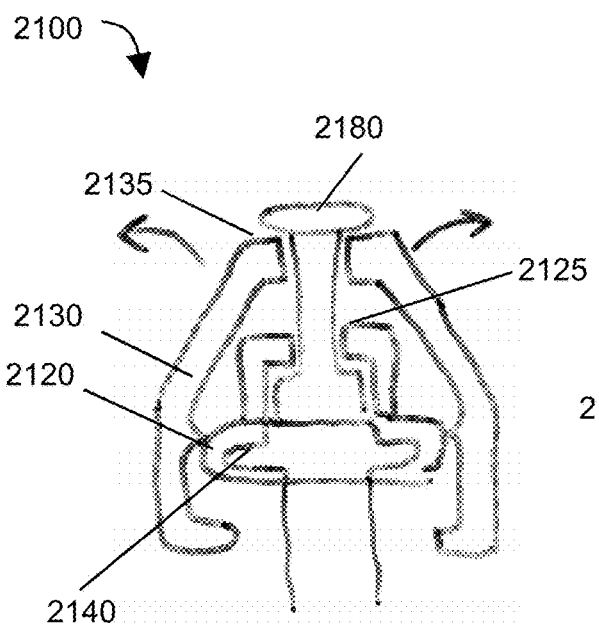
FIGS. 21A-B show a hinged device that attaches to a finger flange.
Figure 21B:
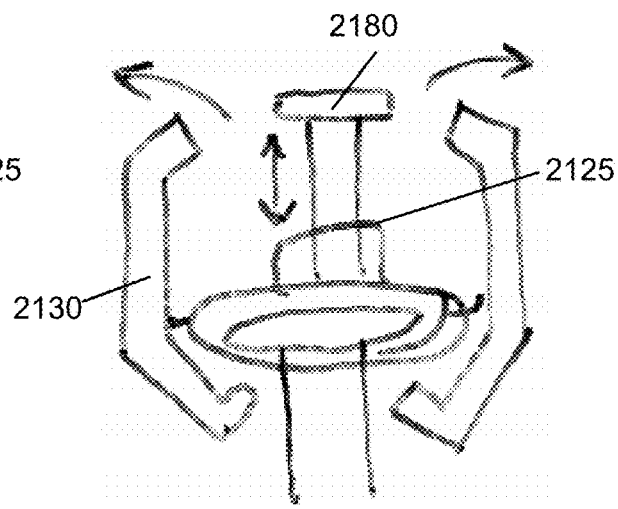

Another embodiment is shown in FIGS. 21A-B, wherein a hinged device 2100 is attached to the finger flange 2140. The hinged device has a stable portion 2120 with a bearing surface 2125 and one or more moveable arms 2130 with bearing surfaces 2135. The hinged device 2100 can assume a first configuration where the arms are folded in, shown in FIG. 21A, such that the bearing surfaces 2135 stop the movement of the plunger 2180 at a first position. The hinged device can then assume a second position by splaying the arms 2130 outward. In the second position, the plunger 2180 can be depressed until it contacts the stable bearing surface 2125. The distance between the first and second positions corresponds to a precise dosage volume.

Figure 22A:
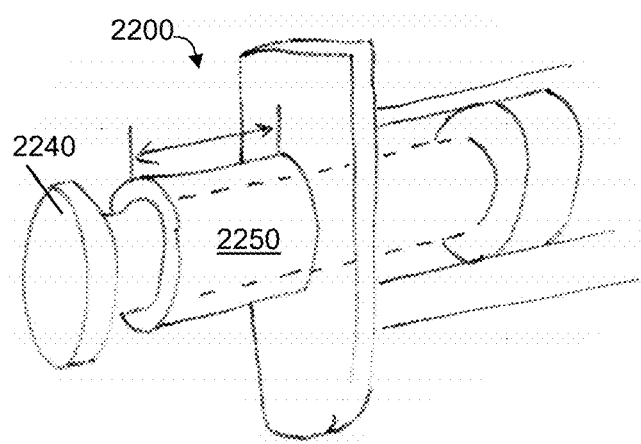
FIGS. 22A-B show a device having an elastomeric sleeve that can be compressed.
Figure 22B:
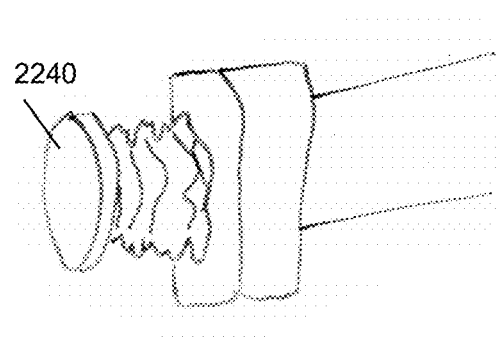

FIGS. 22A-B show an embodiment of a plunger rod stop device 2200 having an elastomeric sleeve 2250 that can be compressed. The plunger 2240 can be depressed until it contacts the elastomeric sleeve 2250 in its non-compressed conformation, and then fully depressed to collapse the sleeve 2250, as shown in FIG. 22B. The difference in length between the compressed and non-compressed conformations is determinative of the dosage volume.

Figure 23A:
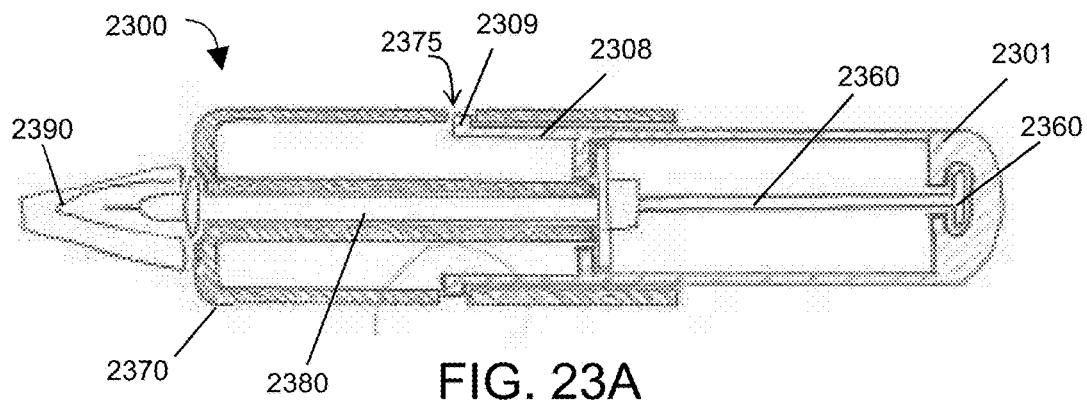
FIGS. 23A-C show a plunger rod stop device with a pin that moves through a track to control the movement of the plunger.
Figure 23B:
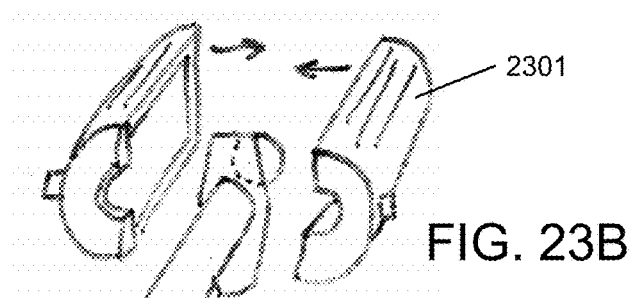
Figure 23C:
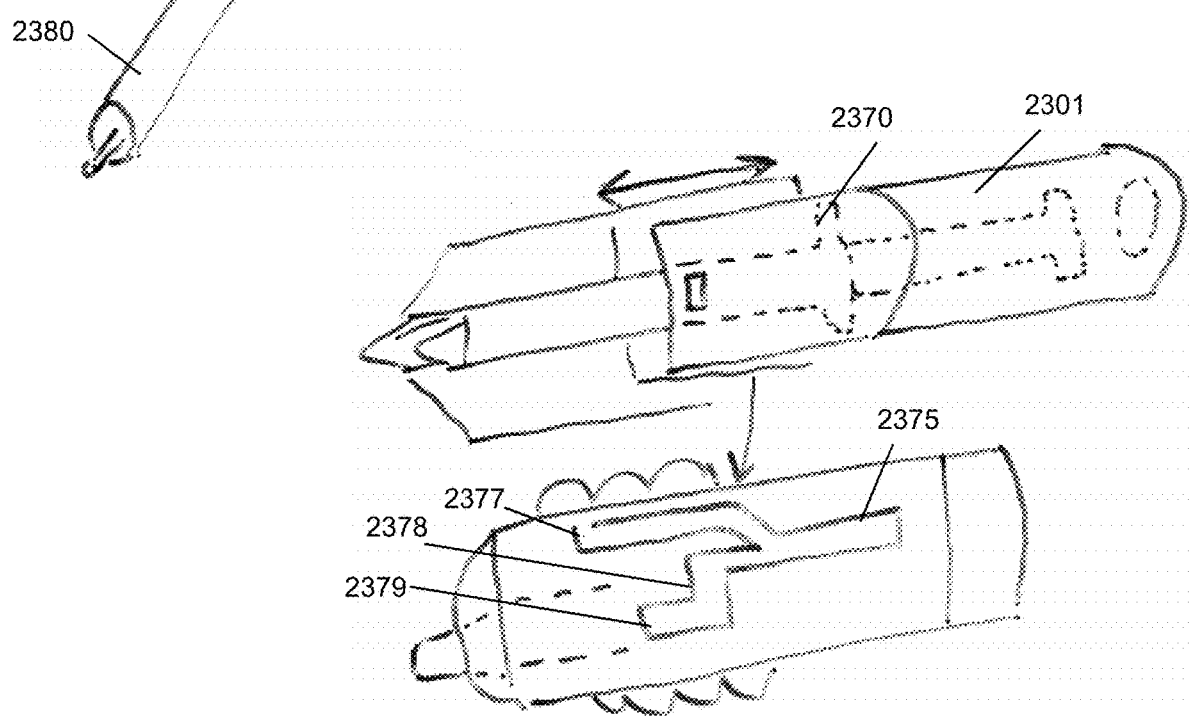

FIG. 23A shows a cross-section of another embodiment of a plunger rod stop device. The device 2300 includes a proximal enclosure 2301 that fits over the plunger rod 2360 and encases the plunger 2365. An optional protective cap 2390 fits over the needle. An exploded view of the proximal enclosure 2301 attaching over the plunger rod is shown in FIG. 23B. In use, the proximal enclosure 2301 is translatable down the length of the barrel to allow the plunger to be advanced. The device 2300 also has an outer shell 2370 that fits immovably around the barrel of the syringe. The proximal enclosure 2301 fits mostly within the lumen of the outer shell 2370 and when the plunger 2360 is advanced, the proximal enclosure 2301 slides further into the outer shell 2370, as shown in FIG. 23C. The proximal enclosure includes at least one extension arm 2308 extending distally and having a pin 2309 that fits into a track 2375 in the outer shell. An example of the track 2375 is shown in FIG. 23C. The track 2375 has multiple stops 2377, 2378, and 2379. When the proximal enclosure is advanced, thereby depressing the plunger, the pin 2309 slides through the track 2375 and bears against one of the stops, preventing the plunger from depressing further. The user can depress the plunger by advancing the proximal enclosure 2301 and guide the pin 2309 into the desired stop 2377-2379 in order to release a desired dosage volume corresponding to that stop. In various embodiments, the track 2375 can have different patterns, such as a stair-step pattern, and various numbers of stops to provide a range of dosages.

Figure 24:
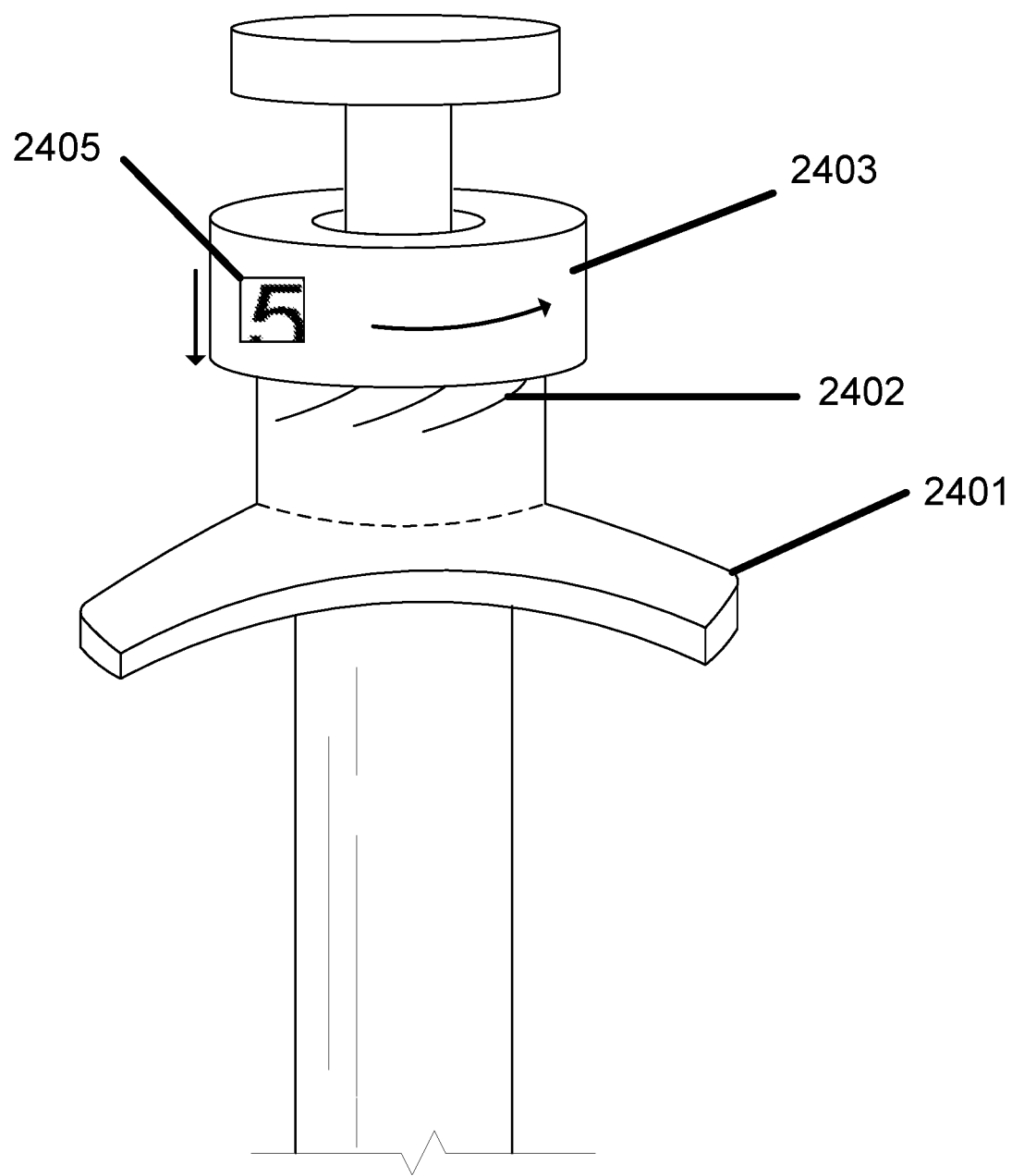
FIG. 24 shows a device with a dial for adjusting dosage.

FIG. 24 shows another embodiment with a dial for adjusting dosage. A finger flange attachment 2401 includes a threaded region 2402 for receiving a dial 2403. The dial 2403 has a window 2405 that reveals the dosage volume as it is turned. The user can dial in the desired dosage, and then depress the plunger until it contacts the upper surface of the dial 2403. In certain embodiments, the entire finger flange is configured to be rotated on a threaded syringe end.

Figures 25A, 25B:
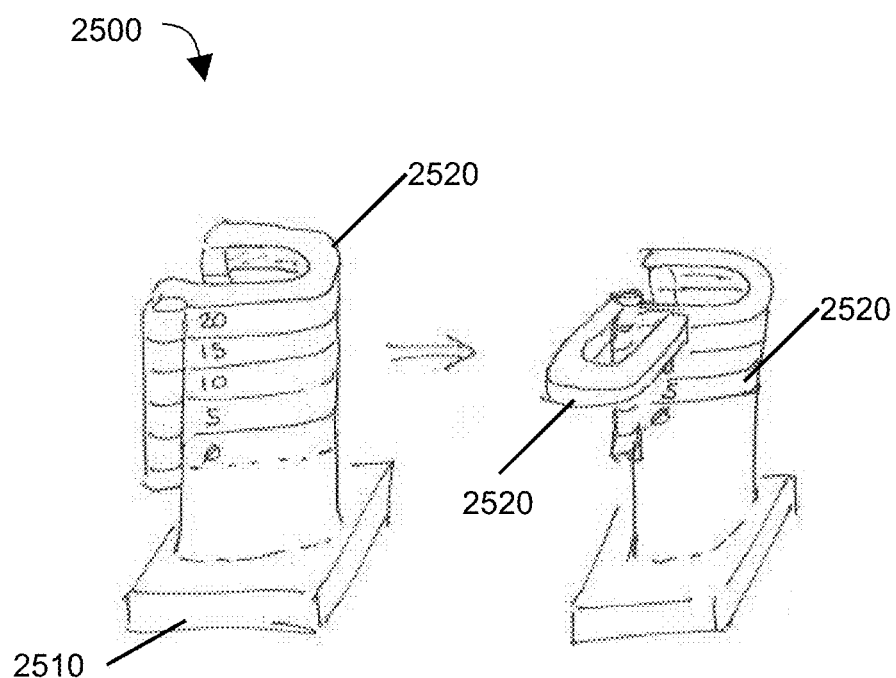
FIGS. 25A-B show a plunger rod stop device with a base and several removable rings.

FIGS. 25A-B show a plunger rod stop device 2500 with a base 2510 and several removable rings 2520. The device 2500 fits around the plunger rod (not shown) of a standard syringe, while the base 2510 bears against the finger flange (not shown). When the device 2500 is attached and the plunger is depressed, the plunger can be advanced only until it contacts the uppermost ring, at which point the range of motion of the plunger is impeded. The rings 2520 are connected to a hinge, so that one or more can be pulled out. A dosage can be measured by the difference between the plunger's resting position and the point at which it connects with one of the rings; or a user can administer a dosage based on the difference between one or more rings. In the example shown, each ring corresponds to an increment of 5 µl. To administer a dosage of 15 µl, for example, a user could depress the plunger until it reaches the top ring, then insert the needle into the patient, pull out three rings, and depress the plunger again, thereby releasing a dosage volume of 15 µl.

Figures 26A, 26B:
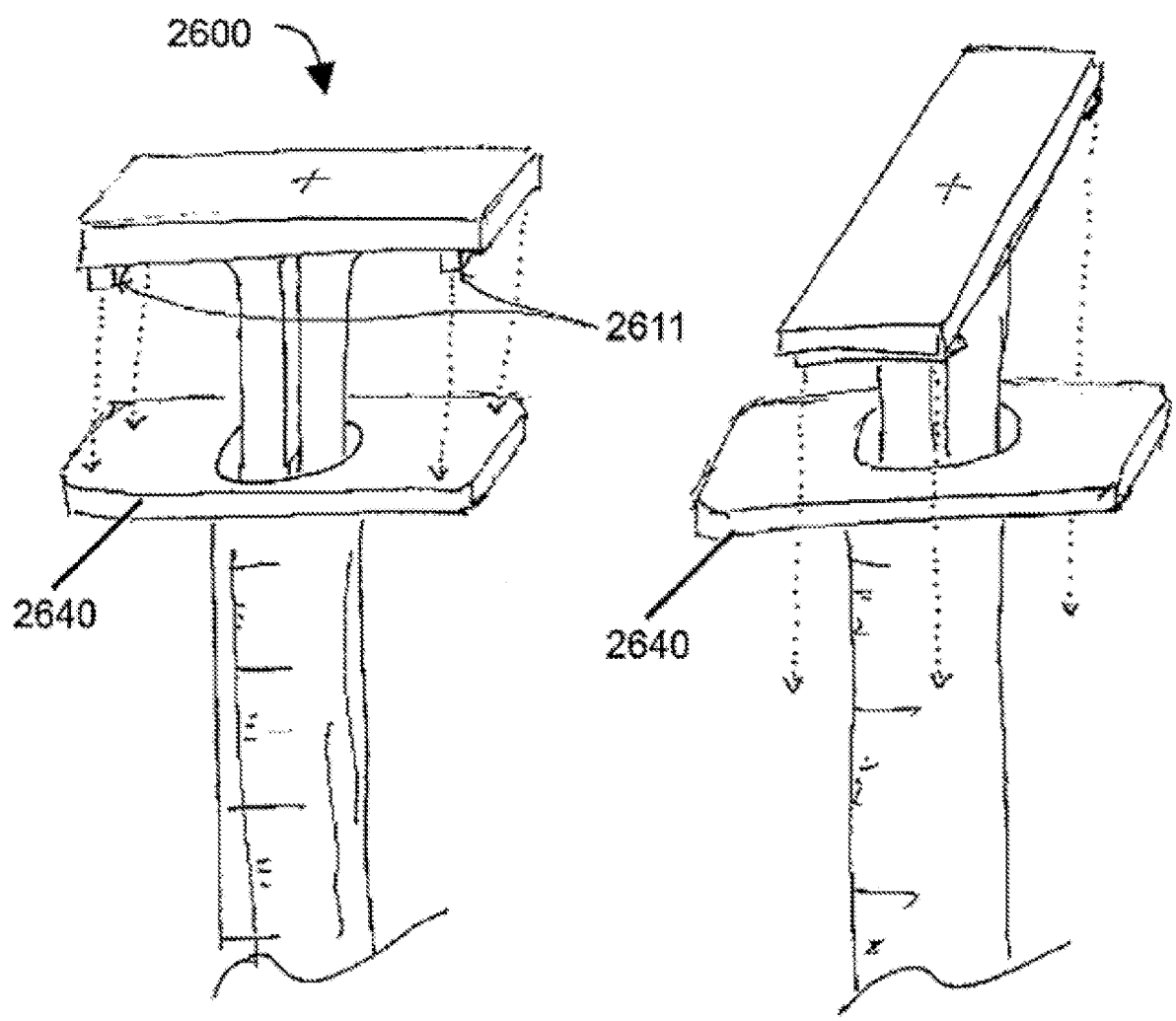
FIGS. 26A-B show a plunger rod stop device that includes a plurality of stand-offs.

FIGS. 26A-B show an embodiment of a plunger rod stop device 2600 that includes a plurality of stand-offs 2611. The device 2600 attaches to the plunger end of a standard syringe and has a similar size and shape to the finger flange 2640, so that when aligned with the finger flange 2640, the stand-offs 2611 contact the upper surface of the finger flange 2640 when the plunger is depressed. To use the device 2600, a user can withdraw a volume of liquid from a vial with the syringe either before or after attaching the device to the plunger. With the device attached, the user aligns the device 2600 and the finger flange 2640 and may invert and expel air or excess liquid from the syringe. The plunger is then depressed all the way until the stand-offs 2611 contact the finger flange 2640. The stand-offs 2611 can be any length up to about the length of the fully withdrawn plunger. As shown in FIG. 26B, the device 2600 is then rotated about 90 degrees so that the stand-offs 2611 no longer contact the finger flange 2640. The plunger can then be advanced until the plunger is fully depressed.

Figures 27A, 27B:
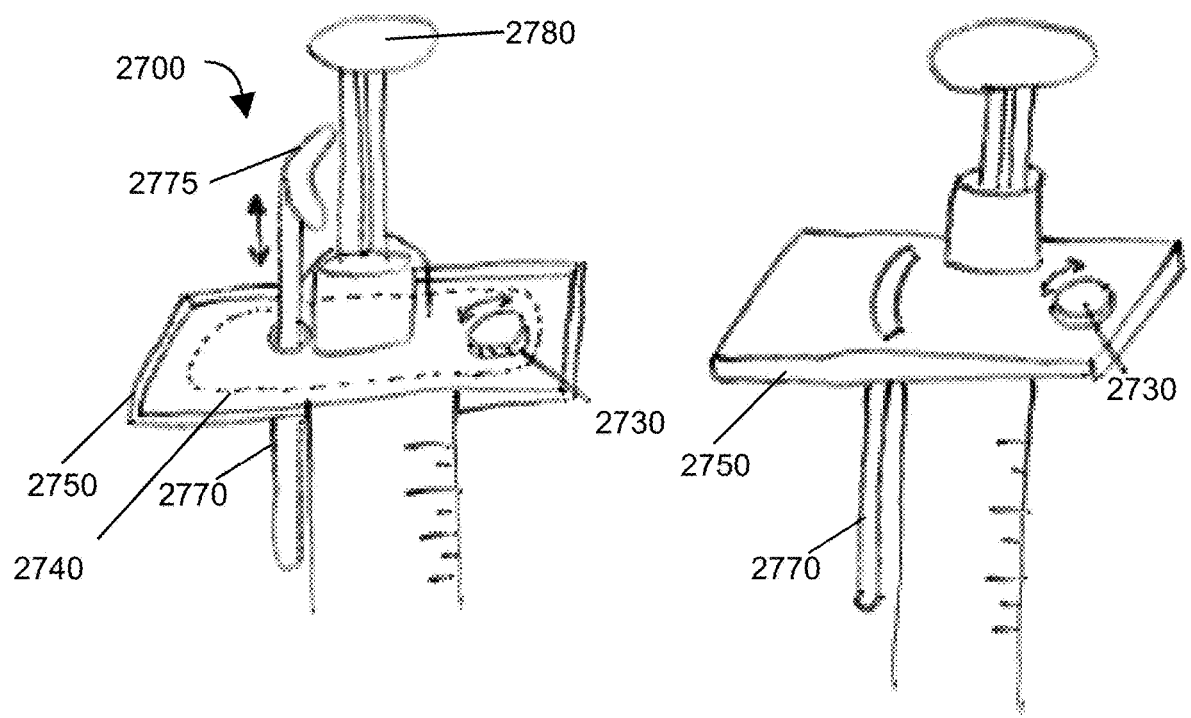
FIGS. 27A-B show a device with an adjustable post.

FIGS. 27A-B show an embodiment wherein a flange attachment 2700 is connected to and covers the finger flange 2740. The flange attachment 2700 includes a platform 2750, a dial 2730, and a post 2770 that fits through an opening in the platform 2750. The platform 2750 also serves to augment the area that the user can hold the finger flange 2740, providing additional control. On the platform 2750 is a dial 2730 that can be rotated to move the post 2770 up and down. The post 2770 can be connected with a ratcheting mechanism or teeth that connect to an internal gear that translates the post as the dial 2730 turns. The dial 2730 may be rotatable in increments of 5 µl. Once a desired dose is dialed in, the plunger 2780 is depressed until it bottoms out on the collar 2775 located at the top of the post 2770. The dial 2730 can then be set to another position, and the plunger advanced again. The distance between the two positions corresponds to the delivered dosage. As shown in FIG. 27B, the post 2770 can be dialed down completely to allow the plunger 2780 to be advanced all the way down, allowing the entire remaining contents of the barrel to be discharged.

FIGS. 28A-30B show several plunger rod stop devices that have a base that attaches to the finger flange and one or more elongated elements that extend toward the plunger. The end of the elongated elements provide a first stop for the plunger to meet, and they can be removed or bent out of the way to expose a second stop.

FIGS. 28A-B provide one such example, having a platform 2810 with two elongated elements 2820 extending toward the plunger 2840. The elongated elements 2820 are rigidly connected to the platform 2810. The elongated elements 2820 have two (or more) stops 2821 and 2822 along their length, which are configured to catch the plunger 2840 and prevent it from advancing further. Adjacent to stops 2822 is a perforation 2828 (shown in FIG. 28B), which allows the upper portion 2829 of the elongated element 2820 to be removed after the plunger 2840 contacts the first set of stops 2821. Once the upper portion 2829 is removed, the plunger 2840 is free to be advanced to the next set of stops 2822. In some embodiments, the elongated elements 2820 have multiple sets of stops and multiple areas of perforation, allowing the device to deliver multiple doses in succession.

Figure 29A:
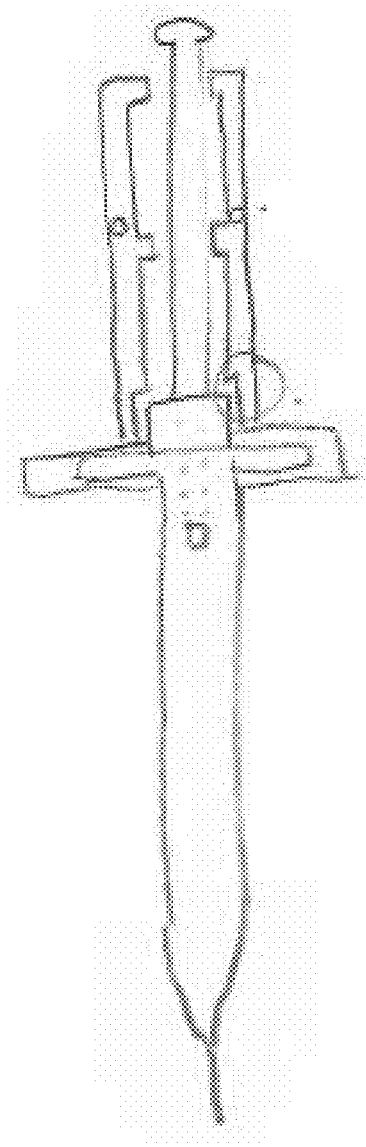
Figure 29B:
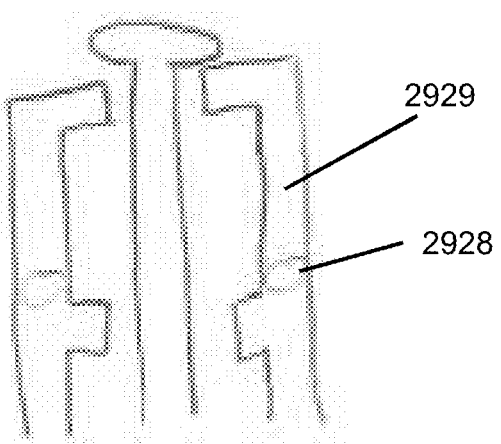

A similar embodiment is shown in FIGS. 29A-B, but instead of perforation that allows the upper portion of the elongated elements to be removed, device 2900 has a flexible material at regions 2928, which allows the upper portion to be bent out of the way after the plunger meets the first stop. After bending the upper portion, the plunger can be advanced to the next stop.

Figure 30:
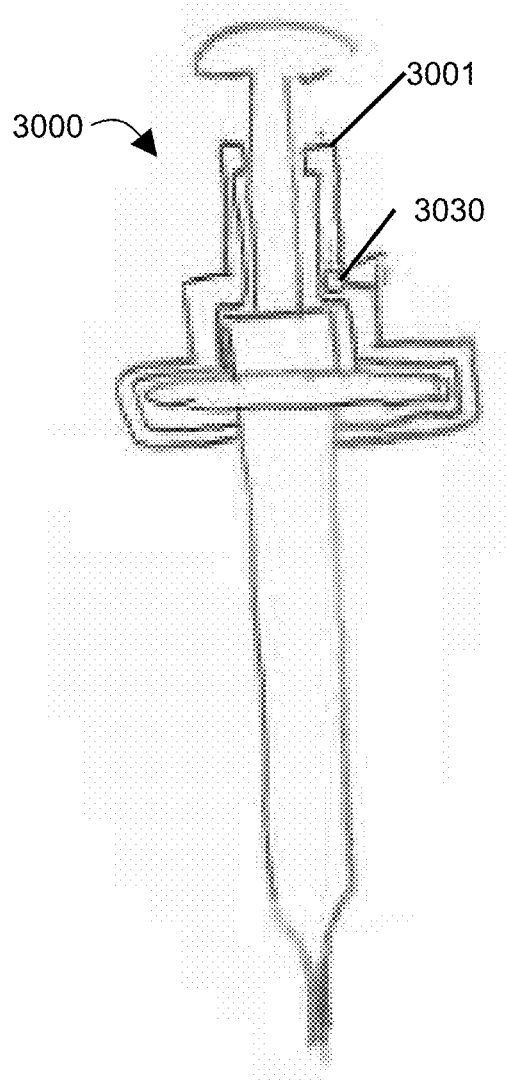
FIGS. 30 and 31 show a plunger rod stop device with a single stop.
Figure 31:
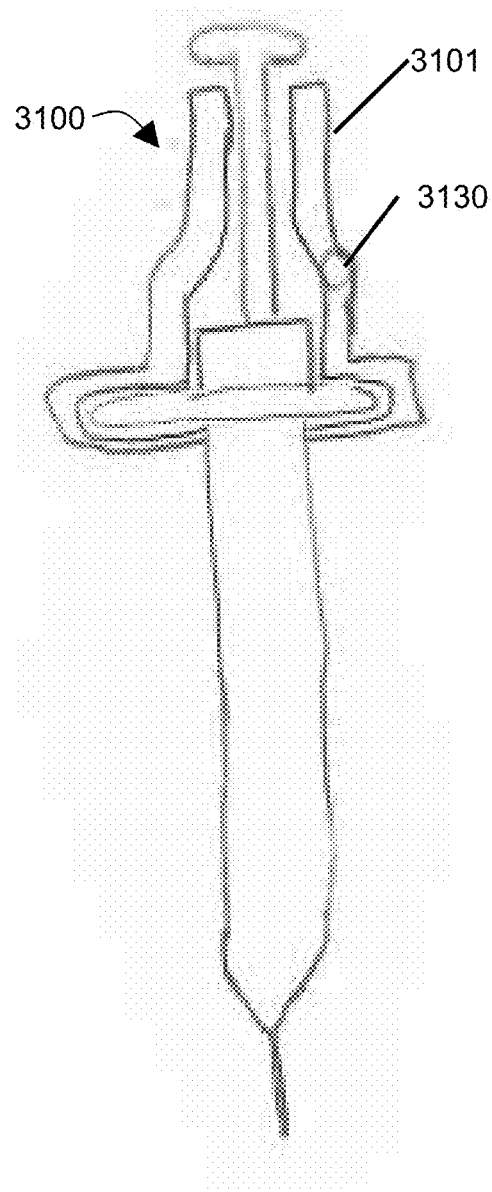

One-stop embodiments are shown in FIGS. 30 and 31. In FIG. 30, the plunger rod stop device 3000 uses a "one-stop" clip with a perforated material at region 3030. The user would use one clip and expel air from the syringe while inverted by advancing the plunger to the priming point 3001. Then the user would snap the upper portion of the elongated element at the perforation 3030, allowing the plunger to advance further. FIG. 31 shows a similar "one-stop" clip with a flexible material at the bend point 3130. Like the prior embodiment, the user expels air from the syringe while inverted by advancing the plunger to the priming point 3101. Then the user bends the upper portion of the elongated element at the bend point 3130.

The embodiment of FIGS. 32A-D relies on a syringe with a "half-moon" or similarly shaped plunger 3240 (shown in side view in FIGS. 32A-D). The plunger rod stop attachment 3210 includes a first elongated element 3220 having a first length and a second elongated element 3230 having a second length. The plunger rod 3250 can be rotated to align the half-moon shaped plunger 3240 with one or the other elongated element. The distalmost point on the first elongated element 3220 is the priming location 3225, and the corresponding point on the second elongated element 3230 is the dosing location 3235. To operate the device, the syringe is inverted, as shown in FIG. 32B, and with the plunger 3240 aligned with the first elongated element 3220, the plunger 3240 is depressed until it contacts the priming location 3225, to eliminate air trapped in the syringe. Next, as shown in FIG. 32C, the syringe is inverted again and the plunger rod is rotated 180 degrees so that the plunger 3240 is no longer in contact with the priming location 3225. Finally, as shown in FIG. 32D, the plunger is depressed until it contacts the dosing location 3235. The distance the plunger travels between the priming location 3225 and the dosing location 3235 defines the dosage amount delivered.

Another plunger rod stop device is shown in FIGS. 33A-F. The device 3300 attaches to the barrel or finger flange of a syringe, and has a shaft 3301 that runs parallel to the plunger rod 3302. A stop 3305 at the end of the shaft 3301 is shaped to catch the plunger and prevent it from advancing. The device 3300 functions as a micrometer, with a dial 3315 that can be turned to advance or withdraw the shaft 3301. The dial 3315 may have an auditory or tactile feedback feature to notify a user when the shaft has advanced a particular unit. For example, there may be an audible click when the shaft 3301 advances by a length corresponding to a 5 µl change in the dosage volume.

Figure 33A:
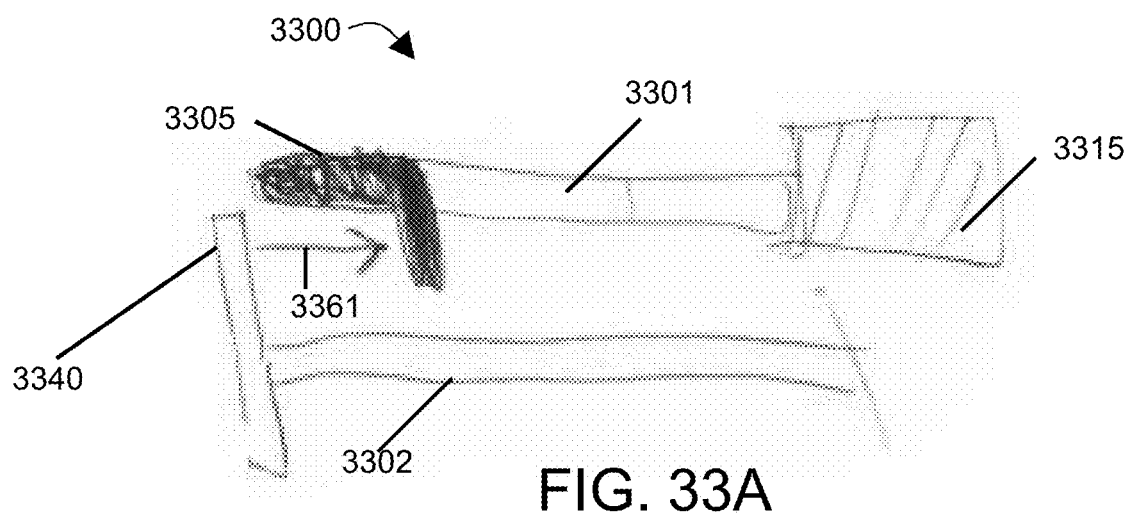
FIGS. 33A-F show a plunger rod stop device and steps for using it.
Figure 33B:
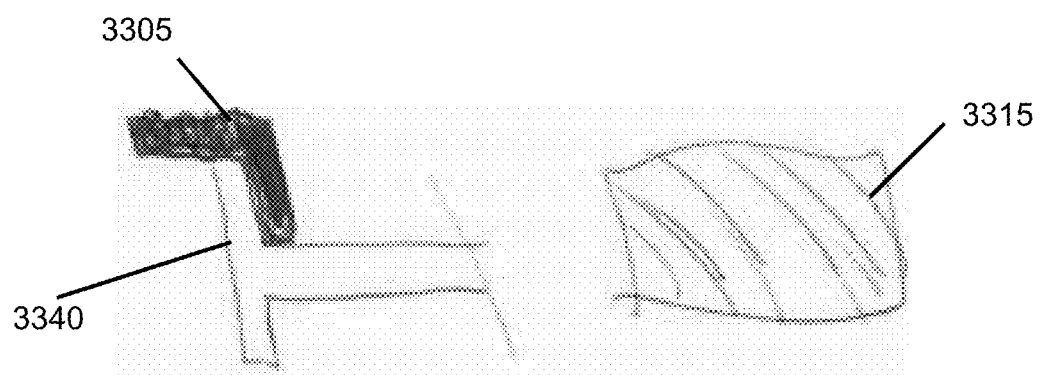
Figure 33C:
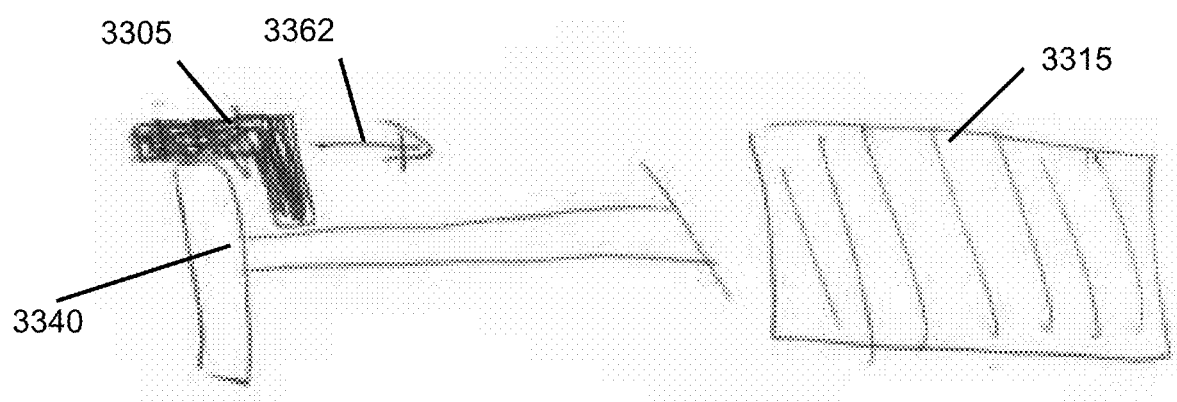
Figure 33D:
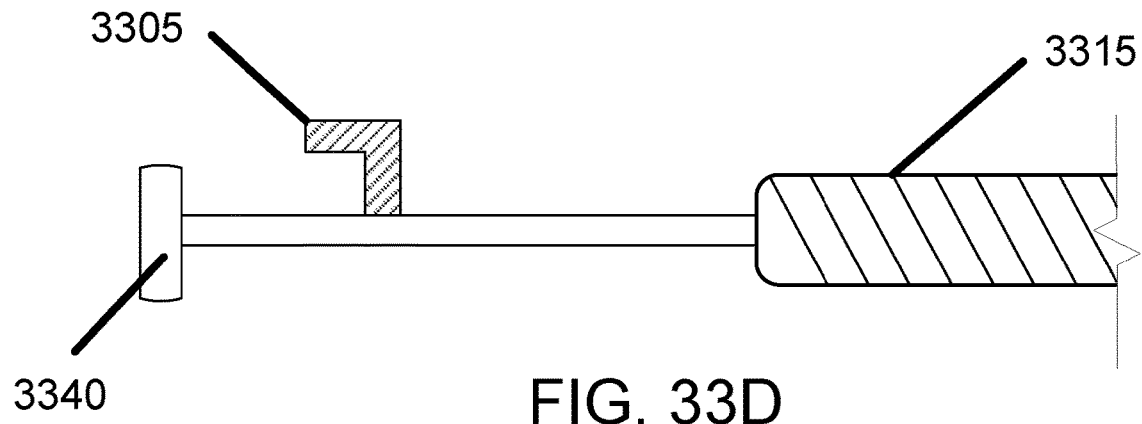
Figure 33E:
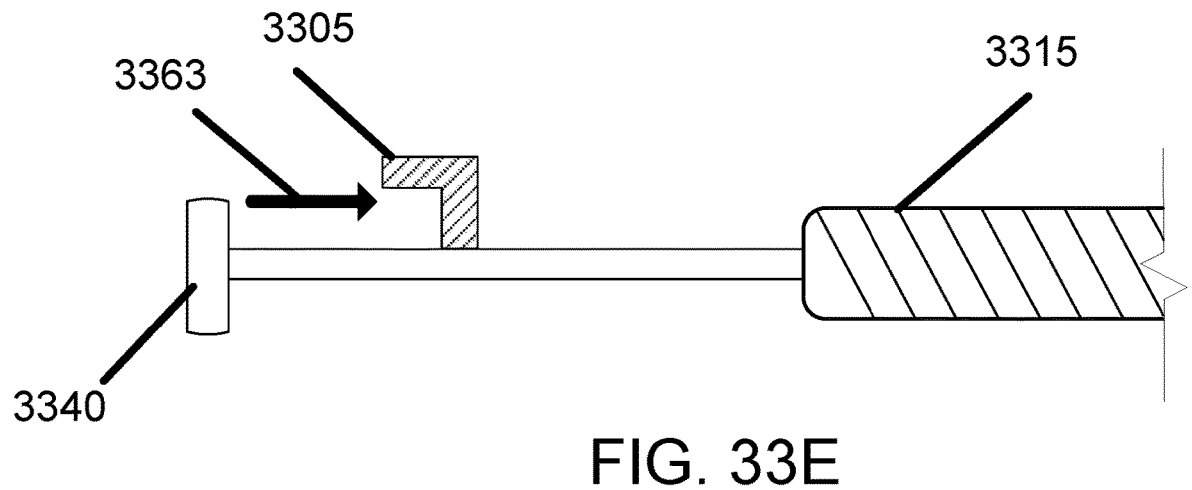
Figure 33F:
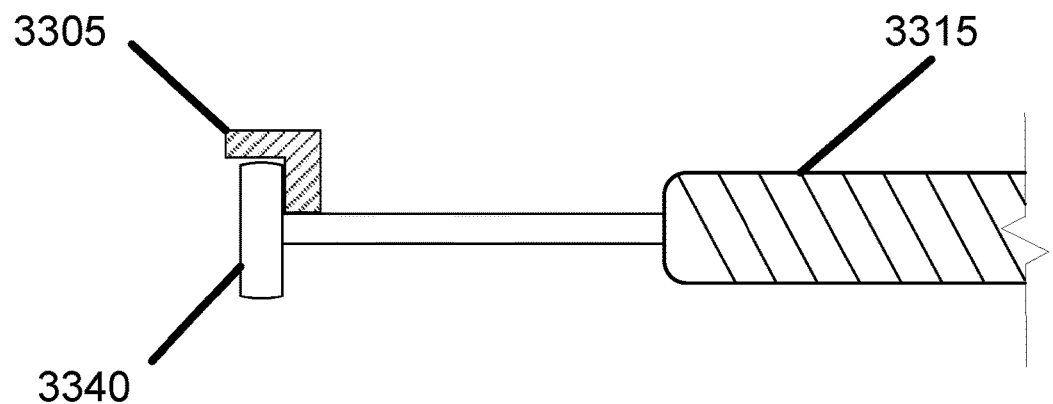

The steps for using the micrometer device 3300 are shown in FIGS. 33A-F. In a first step, the shaft 3301 is at a baseline position, and the plunger 3340 is advanced until it contacts the stop 3305 as indicated by arrow 3361, to expel air from the syringe. FIG. 33B shows the plunger 3340 contacting the stop 3305 in the baseline position. In FIG. 33C, the dial 3315 is turned, causing the stop 3305 to move in the direction of arrow 3362, after which the stop 3305 reaches a new position as shown in FIG. 33D. The plunger 3340 is then depressed, as indicated by arrow 3363 in FIG. 33E. The plunger 3340 bottoms out against the stop 3305 once again, as shown in FIG. 33F, to deliver the corresponding dosage.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

Any and all references and citations to other documents, such as patents, patent applications, patent publications, journals, books, papers, and web contents, which have been made throughout this disclosure, are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A plunger rod stop device for modifying a syringe, the plunger rod stop device comprising:
   a cylindrical body configured to attach to a plunger of the syringe and comprising:
      a horizontal slot sized to removably capture the plunger and being disposed in an outer radial surface of the cylindrical body, a width of the horizontal slot extending only a portion of a circumference of the outer radial surface; and
      a vertical recess disposed along the outer radial surface of the cylindrical body and sized to receive the plunger, the vertical recess being narrower than the width of the horizontal slot and extending from and orthogonal to the horizontal slot to an end of the cylindrical body proximate a stand-off; and
   the stand-off extending from the cylindrical body, the stand-off configured to contact a fixed element on the syringe to prevent the plunger from being depressed all the way when the plunger rod stop device is attached to the plunger in a first orientation with respect to the syringe,
   wherein the plunger rod stop device can be rotated to a second orientation to allow the plunger to be depressed to expel a predetermined amount of liquid from the syringe.

2. The plunger rod stop device of claim 1, wherein the fixed element is a finger flange of the syringe.

3. The plunger rod stop device of claim 1, wherein the fixed element is a barrel of the syringe.

4. The plunger rod stop device of claim 1, wherein the cylindrical body comprises a resilient material.

5. The plunger rod stop device of claim 4, wherein the resilient material is a resin.

6. The plunger rod stop device of claim 1, wherein the vertical recess comprises a snap fitting for securing the plunger.

7. The plunger rod stop device of claim 1, wherein the stand-off is molded to the cylindrical body.

8. The plunger rod stop device of claim 1, further comprising a second stand-off.

9. The plunger rod stop device of claim 1, wherein the predetermined amount of liquid corresponding to a distance between an edge of the stand-off and the cylindrical body.

10. The plunger rod stop device of claim 1, wherein the horizontal slot comprises a crush rib.

\* \* \* \* \*